US009428557B2

(12) United States Patent
Ensoli et al.

(10) Patent No.: US 9,428,557 B2
(45) Date of Patent: Aug. 30, 2016

(54) PROCESS FOR THE PRODUCTION OF BIOLOGICALLY ACTIVE HIV-1 TAT PROTEIN

(75) Inventors: Barbara Ensoli, Rome (IT); Mauro Magnani, Torre San Tommaso (IT)

(73) Assignees: ISTITUTO SUPERIORE DI SANITA, Rome (IT); UNIVERSITA DEGLI STUDI DI URBINO, Urbino Pu (IT)

( * ) Notice: Subject to any disclaimer, the term of this patent is extended or adjusted under 35 U.S.C. 154(b) by 208 days.

(21) Appl. No.: 12/866,714

(22) PCT Filed: Feb. 6, 2009

(86) PCT No.: PCT/EP2009/001198
§ 371 (c)(1),
(2), (4) Date: Dec. 14, 2010

(87) PCT Pub. No.: WO2009/098094
PCT Pub. Date: Aug. 13, 2009

(65) Prior Publication Data
US 2011/0319593 A1 Dec. 29, 2011

(30) Foreign Application Priority Data
Feb. 6, 2008 (GB) .................................. 0802224.6

(51) Int. Cl.
  C12P 21/02 (2006.01)
  C07K 14/15 (2006.01)
  A61K 35/00 (2006.01)
  A61K 39/21 (2006.01)
  C07K 14/155 (2006.01)
  C07K 14/16 (2006.01)
  C07K 14/005 (2006.01)
  A61K 38/16 (2006.01)
  A61K 39/00 (2006.01)

(52) U.S. Cl.
  CPC ........... C07K 14/163 (2013.01); C07K 14/005 (2013.01); A61K 38/162 (2013.01); A61K 39/00 (2013.01); A61K 39/21 (2013.01); C07K 14/15 (2013.01); C07K 14/155 (2013.01); C07K 14/16 (2013.01); C07K 2319/10 (2013.01); C12N 2740/16322 (2013.01)

(58) Field of Classification Search
  CPC ........... A61K 2039/525; A61K 39/12; A61K 2039/6075; C07K 14/005; C07K 7/08; C12N 15/86; C12N 7/00; C12N 15/70; C12N 2810/6054; C12N 2740/16022; C12N 2740/16034; C12N 2740/16051; C12N 2740/16061; C12N 2740/16211; C12N 2740/16311
See application file for complete search history.

(56) References Cited

U.S. PATENT DOCUMENTS

| 5,238,822 | A | * | 8/1993 | Dykes et al. | 435/69.1 |
|---|---|---|---|---|---|
| 5,597,895 | A | * | 1/1997 | Gaynor et al. | 530/324 |
| 5,614,385 | A | * | 3/1997 | Oppermann et al. | 435/69.4 |
| 5,712,119 | A | * | 1/1998 | Oppermann et al. | 435/69.4 |
| 5,733,782 | A | * | 3/1998 | Dorai et al. | 435/328 |
| 6,013,432 | A | * | 1/2000 | Luciw et al. | 435/5 |
| 6,013,515 | A | * | 1/2000 | Xiao et al. | 435/320.1 |
| 7,244,814 | B2 | * | 7/2007 | Mathews et al. | 530/300 |
| 7,442,525 | B1 | * | 10/2008 | Luciw et al. | 435/69.7 |
| 7,744,896 | B1 | * | 6/2010 | Ensoli | 424/188.1 |
| 7,811,573 | B2 | * | 10/2010 | Ensoli | 424/184.1 |
| 8,197,820 | B2 | * | 6/2012 | Ensoli | 424/188.1 |
| 2003/0198621 | A1 | * | 10/2003 | Megede et al. | 424/93.2 |
| 2003/0223964 | A1 | * | 12/2003 | Barnett et al. | 424/93.2 |
| 2005/0036985 | A1 | * | 2/2005 | Ensoli | 424/93.2 |
| 2005/0058657 | A1 | * | 3/2005 | Ertl et al. | 424/188.1 |
| 2005/0208482 | A1 | * | 9/2005 | Cohen | 435/5 |
| 2006/0104988 | A1 | * | 5/2006 | Pauza et al. | 424/188.1 |
| 2007/0141557 | A1 | * | 6/2007 | Raab et al. | 435/5 |
| 2007/0248618 | A1 | * | 10/2007 | Cohen | 424/188.1 |
| 2009/0252754 | A1 | * | 10/2009 | Caputo et al. | 424/188.1 |
| 2010/0015087 | A1 | * | 1/2010 | Ensoli | 424/85.2 |

FOREIGN PATENT DOCUMENTS

| EP | 1 279 404 A1 | | 1/2003 |
|---|---|---|---|
| WO | WO 8702989 A1 | * | 5/1987 |
| WO | WO 03009867 A1 | * | 2/2003 |

OTHER PUBLICATIONS

Sim IS. The human immunodeficiency virus TAT protein. A target for antiviral agents. Ann N Y Acad Sci. 1990;616:64-72.*

Siddappa NB, Venkatramanan M, Venkatesh P, Janki MV, Jayasuryan N, Desai A, Ravi V, Ranga U. Transactivation and signaling functions of Tat are not correlated: biological and immunological characterization of HIV-1 subtype-C Tat protein. Retrovirology. Aug. 18, 2006;3:53.*

McKenna MC, Muchardt C, Gaynor R, Eisenberg D. Preparative scale culture of *Escherichia coli* cells expressing the human immunodeficiency virus type 1 Tat protein. Protein Expr Purif. Apr. 1994;5(2):105-11. Erratum in: Protein Expr Purif Aug. 1994;5(4):422.*

Kirsch T, Boehm M, Schuckert O, Metzger AU, Willbold D, Frank RW, Rösch P. Cloning, high-yield expression in *Escherichia coli*, and purification of biologically active HIV-1 Tat protein. Protein Expr Purif. Aug. 1996;8(1):75-84.*

(Continued)

*Primary Examiner* — Rachel B Gill

(74) *Attorney, Agent, or Firm* — Mark S. Cohen; Pearl Cohen Zedek Latzer Baratz LLP

(57) ABSTRACT

Tat protein produced in bulk culture is inactive when induced at conventional optical densities but can be obtained in biologically active form when induced during the logarithmic growth phase.

9 Claims, 7 Drawing Sheets

(56) References Cited

OTHER PUBLICATIONS

Fanales-Belasio E, Moretti S, Nappi F, Barillari G, Micheletti F, Cafaro A, Ensoli B. Native HIV-1 Tat protein targets monocyte-derived dendritic cells and enhances their maturation, function, and antigen-specific T cell responses. J Immunol. Jan. 1, 2002;168(1):197-206.* pET21b vector map. Novagen. Cat. #69741-3.*

E. coli strain BL21 (DE3) genotype description. New England Biolabs. Cat. #C2527H.*

Ramakrishna L, Anand KK, Mohankumar KM, Ranga U. Codon optimization of the tat antigen of human immunodeficiency virus type 1 generates strong immune responses in mice following genetic immunization. J Virol. Sep. 2004;78(17):9174-89.*

Conrad B, Savchenko RS, Breves R, Hofemeister J. A T7 promoter-specific, inducible protein expression system for Bacillus subtilis. Mol Gen Genet. Feb. 5, 1996;250(2):230-6.*

Kraichely DM, MacDonald PN. Confirming yeast two-hybrid protein interactions using in vitro glutathione-S-transferase pulldowns. Methods Mol Biol. 2001;177:135-50.*

Khan F, Legler PM, Mease RM, Duncan EH, Bergmann-Leitner ES, Angov E. Histidine affinity tags affect MSP1(42) structural stability and immunodominance in mice. Biotechnol J. Jan. 2012;7(1):133-47. doi: 10.1002/biot.201100331. Epub Dec. 28, 2011.*

Arnau J, Lauritzen C, Petersen GE, Pedersen J. Current strategies for the use of affinity tags and tag removal for the purification of recombinant proteins. Protein Expr Purif. Jul. 2006;48(1):1-13. Epub Dec. 28, 2005.*

Gaberc-Porekar V, Menart V. Perspectives of immobilized-metal affinity chromatography. J Biochem Biophys Methods. Oct. 30, 2001;49(1-3):335-60.*

Bullok KE, Dyszlewski M, Prior JL, Pica CM, Sharma V, Piwnica-Worms D. Characterization of novel histidine-tagged Tat-peptide complexes dual-labeled with (99m)Tc-tricarbonyl and fluorescein for scintigraphy and fluorescence microscopy. Bioconjug Chem. Nov.-Dec. 2002;13(6):1226-37.*

Compact Lab-Scale 15L Fermentor System, www.equipnet.com, Accessed Apr. 15, 2014.*

Zhou C, Rana TM. A bimolecular mechanism of HIV-1 Tat protein interaction with RNA polymerase II transcription elongation complexes. J Mol Biol. Jul. 26, 2002;320(5):925-42; entire document; abstract; pp. 931-932.*

Saroja Ch, Lakshmi P, Bhaskaran S. Recent trends in vaccine delivery systems: A review. Int J Pharm Investig. Apr. 2011;1(2):64-74.*

Yan W, Jain A, O'Carra R, Woodward JG, Li W, Li G, Nath A, Mumper RJ. Lipid Nanoparticles with Accessible Nickel as a Vaccine Delivery System for Single and Multiple His-tagged HIV Antigens. HIV AIDS (Auckl). Jul. 1, 2009;2009(1):1-11.*

Ensoli B. Criteria for selection of HIV vaccine candidates—general principles. Microbes Infect. Nov. 2005;7(14):1433-5. Epub Sep. 15, 2005.*

Ensoli B, Fiorelli V, Ensoli F, Cafaro A, Titti F, Buttò S, Monini P, Magnani M, Caputo A, Garaci E. Candidate HIV-1 Tat vaccine development: from basic science to clinical trials. AIDS. Nov. 28, 2006;20(18):2245-61.*

Ensoli B, Cafaro A, Caputo A, Fiorelli V, Ensoli F, Gavioli R, Ferrantelli F, Cara A, Titti F, Magnani M. Vaccines based on the native HIV Tat protein and on the combination of Tat and the structural HIV protein variant DeltaV2 Env. Microbes Infect. Nov. 2005;7(14):1392-9. Epub Sep. 15, 2005.*

Aldovini et al., Synthesis of the Complete Trans-activation Gene Product of Human T-lymphotropic Virus Type III in Escherichia Coli: Demonstration of Immunogenicity in Vivo and Expression in Vitro, Proc. Natl. Acad. Sci. USA, Sep. 1986, vol. 83, pp. 6672-6676.

Arya et al., Trans-Activator Gene of Human T-Lymphotropic Virus Type III (HTLV-III), Science, New Series, Jul. 5, 1985. vol. 229, No. 4708, pp. 69-73.

Barillari et al., The Tat Protein of Human Immunodeficiency Virus Type 1, a Growth Factor for AIDS Kaposi Sacroma and Cytokine-Activated Vascular Cells, Induces Adhesion of the Same Cell Types by Using Intergin Receptors Recognizing the RGD Amino Acid Sequence, Proc., Natl, Acad. Sci. USA, Sep. 1993, vol. 90, pp. 7941-7945.

Barillari et al., The Tat Protein of Human Immtmodeficiency Virus Type-1 Promotes Vascular Cell Growth and Locomotion by Engaging the α5β1 and αvβ3 Intergins and by Mobilizing Sequestered Basic Fibroblast Growth Factor, Blood, Jul. 15, 1999, vol. 94, No. 2, pp. 663-672.

Brake et al., Identification of an Arg-Gly-Asp (RDG) Cell Adhesion Site in Human Immunodeficiency Virus Type 1 Transactivation Protein, tat, The Journal of Cell Biology, Sep. 1990, vol. 111, pp. 1275-1281.

Burton, A Vaccine for HIV Type 1: The Antibody Perspective, Proc. Natl. Acad. Sci. USA, Sep. 1997, vol. 94, pp. 10018-10023.

Butto et al., Sequence Conversation and Antibody Cross-Recognition of Clade B Human Immunodeficiency Virus (HIV) Type 1 Tat Protein in HIV-1-Infected Italians, Ugandans and South Africans, The Journal of Infectious Diseases, 2003, vol. 188, pp. 1171-1180.

Cafaro et al., SHIV89.6P Pathogencity in Cynomolgus Monkeys and Control of the Viral Replication and Disease Onset by Human Immunodeficiency Virus Type 1 Tat Vaccine, J Med Primarol, 2000, vol. 29, pp. 193-208.

Cafaro et al., Vaccination with DNA Containing tat Coding Sequences and Unmethylated CpG Motifs Protects Cynomolgus Monkeys Upon Infection with Simian/Human Immunodeficiency Virus (SHIV89.6P), Vaccine, 2001, vol. 19, pp. 2862-2877.

Cafaro at at, Control of SHIV-89-6P-Infection of Cynomolgus Monkeys by HIV-1 Tat Protein Vaccine, Nature Medicine, Jun. 1999, vol. 5, pp. 643-650.

Demirhan et al., Antibody Spectrum the Viral Transactivator Protein in Patients with Human Immunodeficiency Virus Type 1 Infection and Kaposi's Sarcoma, Journal of Virology May/Jun. 2000,vol. 3, pp. 137-143.

Ensoli et al., Tat Protein of HIV-1 Stimulates Growth of Cells Derived from Kaposi's Sarcoma Lesions of AIDS Patients, Nature, May 1990, vol. 345, pp. 84-86.

Ensoli et al., Cytokines and Growth Factors in the Pathogenesis of AIDS-ASSOCIATED Kaposi's Sarcoma, Immunological Reviews 1992, No. 127, pp. 146-155.

Ensoli et al., Release, Uptake, and Effects of Extracelluar Human Immunodeficiency Virus Type 1 Tat Protein on Cell Growth and Viral Transactivation, J. Virol, 1993, vol. 62, No. 1, p. 277-287.

Ensoli et al., Synergy Between Basic Fibroblast Growth Factor and HIV-1 Tat Protein in Induction of Kaposi's Sarcoma, Nature, Oct. 20, 1994, vol. 371, pp. 674-680.

Fanales-Belasio et al., Native HIV-1 Tar Protein Targets Monocyte-Derived Dendritic Cells and Enhances Their Maturation, Function, and Antigen-Specific T Cell Responses, J Immunol, 2002, vol. 168, pp. 197-206.

Fisher et al., The Trans-Activator Gene of HTLV-III is Essential for Virus Replication, Nature, Mar. 27, 1986, vol. 320, pp. 367-371.

Frankel et al., Cellular Uptake of the Tat Protein from Human Immunodeficiency Virus, Cell, Dec. 23, 1988, vol. 55, pp. 1189-1191.

Gavioli et al., 1-I1V-1 Tat Protein Modulates the Generationof Cytotoxic T Cell Epitopes by Modifying Proteasome Composition and Enzymatic Activity, J Immunol 2004, vol. 173, pp. 3838-3843.

Hauber. et al., Mutational Analysis of the Conserved Basic Domain of Human Immunodeficiency Virus Tat Protein, J. Virol. Mar. 1989, vol. 63, No. 3, pp. 1181-1187.

Kim et al., Introduction of Soluble Proteins intothe MHC Class I Pathway by Conjugation to an HIV tat Peptide, The Journal of Immunology, 1997, vol. 159, pp. 1666-1668.

Lifson et al., The Extent of Early Viral Replication is a Critical Determinant of the Natural History of Simian Immunodeficiency Virus Infection, Journal of Virology, Dec. 1997, vol. 71, No. 12, pp. 9508-9514.

Maggiorella et al., Long-term Protection Against SHIV89.6P Replication in HIV-1 Tat Vaccinated Cynomolgus Monkeys, Vaccine, 2004, vol. 22, pp. 3258-3269.

(56) References Cited

OTHER PUBLICATIONS

Mellors et al., Prognosis in HIV-1 Infection Predicted by the Quantity of Virus in Plasma, Science, May 24, 1996, vol. 272, pp. 1167-1170.
Moy et al., Tat-Mediated Protein Delivery Can Facilitate MHC Class I Presentation of Antigens, Molecular Biotechnology, 1996, vol. 6, pp. 105-113.
Ratner et al., Complete Nucleotide Sequence of the AIDS Virus, HTLV-III, Nature, Jan. 24, 1985, pp. 277.
Rezza et al., The Presence of Anti-Tat Antibodies is Predictive of Long-Term Nonprogression to AIDS or Severe Immunodeficiency: Findings in a Cohort of HIV-1 Seroconverters, Erief Report, Apr. 15, 2005, pp. 1321-1324.
Rodman et al., Epitopes for Natural Antibodies of Human Immunodeficiency Virus (HIV)-negative (normal) and HIV-positive Sera are Coincident with Two Key Functional Sequences of HIV Tat Protein, Proc. Natl. Acad. Sci USA, Aug. 1993, pp. 7719-7723.
Rosenberg et al., Vectors for Selective Expression of Cloned DNAs by T7 RNA Polymerase, Gene, 1987, vol. 56, pp. 125-135.
Roy et al., A Bulge Structure in HIV-1 TAR RNA is Required for Tat Binding and Tat-mediated Trans-activation, Genes Dev., 1990, vol. 4, pp. 1365-1373.
Ruben et al, Structural and Functional Characterization of Human Immunodeficiency Virus tat Protein, Journal of Virology, Jan. 1989, vol. 63, No. 1, pp. 1-8.
Seigel et al., Transactivation Induced by Human T-Lymphotropic Virus Type III (HTLV III) Maps to a Viral Sequence Encodiing 58 Amino Acids and Lacks Tissue Specificity, Virology, 1986, vol. 148, pp. 226-231.
Sodroski et al., Location of Trans-Activating Region on the Genome of Human T-Cell Lymphotropic Virus Type III, Science New Series, Jul. 5, 1985, vol. 229, No. 4708, pp. 74-77.
Staprans et al., Simian Immunodeficiency Virus Disease Course is Predicted by the Extent of Virus Replication During Primary Infection, Journal of Virology, Jun. 1999, vol. 73, No. 6 pp. 4829-4839.
Studier et al. Use of Bacteriophage T7 RNA Polymerase to Direct Selective High-level Expression of Cloned Genes, J. Mol. Biol. 1989, vol. 189, pp. 113-130.
Studier et al., Use of T7 RNA Polymersase to Direct Expression of Cloned Genes, Methods of Enzymology, vol. 185, 1990, pp. 60-89.
Hafft et al., A Pathogenic Threshold of Virus Load Defined in Simian Immunodeficiency Virus—or Simian-Human Immunodeficiency Virus-Infected Macaques, Journal of Virology, Dec. 1998, pp. 10281-10285.
Tyagi et al., Internalization of HIV-1 Tat Requires Cell Surface Heparan Sulfate Proteoglycans, vol. 276, No. 5, pp. 3254-3261. Oct. 6, 2000.
Wahren et al., HIV Subtypes and Recombination Strains-Strategies for Induction of Immune Responses in Man, Vaccine, vol. 20, 2002, pp. 1988-1993.
Watson et al , Plasma Viremia in Macaques Infected with Simian Immunodeficiency Virus: Plasma Viral Load Early Infection Predicts Survival, Journal of Virology, Jan. 1997, vol. 71, No. 1, pp. 284-290.
Furlini et al., Effect of Antibody to HIV-1 Tat Protein on Viral Replication in Vitro and Progression of HIV-1 Disease in Vivo, Journal of Acquired Immune Deficiency Syndromes and Human Retrovirology, vol. 10, pp. 408-416. 1995.
Reiss et al., Speed of Progression to AIDS and Degree of Antibody Response to Accessory Gene Products of HIV-1, Journal of Medical Virology, 1990, vol. 30, pp. 163-168.
Wu et al., Selective Transcription and Modulation of Resting T Cell Activity by Preintegrated HIV DNA, Science, 2001, vol. 293, p. 1503.
Zagury et al., Antibodies to the HIV-1 Tat Protein Correlated with Nonprogression to AIDS: A Rationale for the Use of Tat Toxoid as an HIV-1 Vaccine, Journal of Human Virology, May/Jun. 1998, vol. 1, No. 4, pp. 282-292.
Krone et al., Natural Antibodies to HIV-tat Epitopes and Expression of HIV-1 Genes in Vivo, Journal of Medical Virology, 1988, vol. 26, pp. 261-270.
Re et al., Antibodies Against Full-length Tat Protein and Some Low-molecular-weight Tat Peptides Correlate with Low or Undetectable Viral Load in HIV-1 Seropositive Patients, Journal of Clinical Virology, 2001, vol. 21, pp. 81-89.
Sipel et al., Scanning the Database for Recombinant HIV-1 Genomes, Nov. 1995, pp. 35-60.
Foley et al., Global Variation in the HIV-1 V3 Region, Feb. 1996, pp. 77-137.
Lettener et al., A New Genetic Subtype of HIV-1, Dec. 1995, pp. 147-150.
"Process development for production of recombinant human interferon-y expressed in *Escherichia coli*" Khalilzadeh et al., J. Ind. Microbiol. Biotechnol., (2004) 31:63-69.
"Pathogenic Role of Extracellular HIV Tat Protein and Vaccine Research Progress Thereof" Lin JanPing, Foreign Medical Sciences, Section of Immunology (2005)-English Translation Version.
UniProtKB/Swiss-Prot: P69697, disclosed on Aug. 13, 1987.

\* cited by examiner

```
        Xba                              rbs              Nde I
----TCTAGAAATAATTTTGTTTAACTTTAAGAAGGAGATATACATATG------
    BamHI
----GGATCCGGGGCT-------
```

Figure 3

```
TGGGCGACTGAATTGGTGTCGACATAGCAGAATAGGCGTTACTCGACAGA        50

GGAGAGCAAGAAATGGAGCCAGTAGATCCTAGACTAGAGCCCTGGAAGCA        100
            met glu pro val asp pro arg leu glu pro trp lys TCCAGGAAGTCAGCCTAAAACTGCTTGTACCAATTGCTATTGTAAAAAGT        150
his pro gly ser gln pro lys thr ala cys thr asn cys tyr cys lys lys GTTGCTTTCATTGCCAAGTTTGTTTCATAACAAAAGCCTTAGGCATCTCC        200
 cys cys phe his cys gln val cys phe ile thr lys ala leu gly ile ser TATGGCAGGAAGAAGCGGAGACAGCGACGAAGACCTCCTCAAGGCAGTCA       250
  tyr gly arg lys lys arg arg gln arg arg arg pro pro gln gly ser GACTCATCAAGTTTCTCTATCAAAGCAACCCACCTCCCAATCCCGAGGGG       300
 gln thr his gln val ser leu ser lys gln pro thr ser gln ser arg gly ACCCGACAGGCCCGAAGGAATAGAAGAAGAAGGTGGAGAGAGAGACAGAG       350
 asp pro thr gly pro lys glu stop

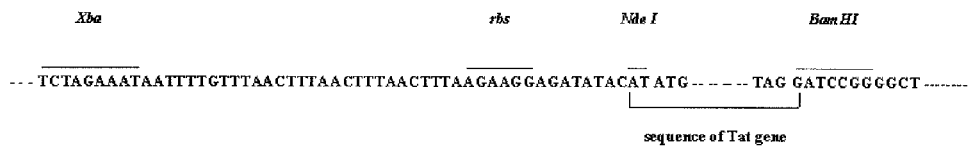

Figure 5

CTTTAAGAAGGAGATATACAT<u>ATGGAGCCAGTAGATCCTAGACTAGAGCC</u>   50
                                 Met glu pro val asp pro arg leu glu pro <u>CTGGAAGCATCCAGGAAGTCAGCCTAAAACTGCTTGTACCAATTGCTATT</u>   100
 trp lys his pro gly ser gln pro lys thr ala cys thr asn cys tyr <u>GTAAAAAGTGTTGCTTTCATTGCCAAGTTTGTTTCATAACAAAAGCCTTA</u>   150
cys lys lys cys cys phe his cys gln val cys phe ile thr lys ala leu <u>GGCATCTCCTATGGCAGGAAGAAGCGGAGACAGCGACGAAGACCTCCTCA</u>   200
gly ile ser tyr gly arg lys lys arg arg gln arg arg arg pro pro gln <u>AGGCAGTCAGACTCATCAAGTTTCTCTATCAAAGCAACCCACCTCCCAAT</u>   250
 gly ser gln thr his gln val ser leu ser lys gln pro thr ser gln <u>CCCGAGGGGACCCGACAGGCCCGAAGGAATAG</u>GGATCCGGCTGCTAACAA   300
ser arg gly asp pro thr gly pro lys glu stop

AGCCCGAAAGGAAGCTGAGTTGGCTGC   327

Figure 6

PROCESS FOR THE PRODUCTION OF BIOLOGICALLY ACTIVE HIV-1 TAT PROTEIN

CROSS-REFERENCE TO RELATED APPLICATIONS

This application is a National Phase Application of PCT International Application PCT/EP2009/001198, filed Feb. 6, 2009, claiming priority to United Kingdom Patent Application GB 0802224.6, filed Feb. 6, 2008, which is incorporated by reference herein in its entirety.

FIELD OF THE INVENTION

The present invention relates to the production of biologically active HIV-1 Tat, derivatives thereof and precursors therefor, including all HIV-1 Glade-specific forms, for use in vaccines.

BACKGROUND OF THE INVENTION

Human Immunodeficiency Virus (HIV), the causative agent of AIDS, continues to spread rapidly throughout the world. WHO and UNAIDS estimate that more than 60 million people have been infected with the virus since the beginning of the epidemic. At the end of 2004 more than 40 million individuals, mostly living in the developing countries, were infected with HIV. The inexorable spreading of the HIV pandemic and the resulting morbidity and mortality arising from AIDS in developing countries underscore the urgency for an effective, safe and inexpensive vaccine against AIDS.

Over the last 15-20 years, most of the efforts in HIV vaccine development have been focused on achieving sterilising immunity by targeting the Envelope protein (Env) of HIV responsible for the binding and entry of the virus, with the rationale of generating neutralising antibodies (NA) capable of protecting against infection (Wahren, 2002). However, results from pre-clinical and clinical trials, including the first phase III trial (AIDSVAX by VaxGen), in which no protection from primary infection in Caucasians has been observed, have been largely disappointing. This can be accounted for by the inability of such vaccines to elicit protective NA, owing to the high variability of Env (Myers, 1995), and hampering the recognition of relevant, mostly conformational, epitopes by the NA, and by the heavy glycosylation of gp120 that contributes to hiding critical (neutralising) env-epitopes (reviewed in Burton 1997).

More recently, other approaches have been developed aimed at inducing T-cell mediated responses against other HIV antigens. These approaches are aimed at controlling virus replication, which is achieved in the absence of sterilising immunity, providing protection from disease progression, and thus reducing virus transmission to healthy individuals. However, these approaches have also failed. An example of this is the recent trial by Merck, based on three HIV genes. This vaccine was created using a mixture of three components, each made with a replication-defective version of one of the common cold viruses, adenovirus type 5 (Ad5), which served as a carrier, or delivery vector, for the HIV gag, pol and nef genes. The vaccine did not prevent infection: in volunteers who received at least one dose of the three-dose vaccine series, 24 cases of HIV infection were observed in the 741 volunteers who received vaccine and 21 cases of HIV infection were observed in the 762 participants in the placebo group. In addition, the vaccine did not reduce the amount of virus in the bloodstream of those who became infected; HIV RNA levels approximately 8 to 12 weeks after diagnosis of infection were similar in the vaccine and the placebo arms.

A radically different approach is based on Tat, a key HIV regulatory gene and its protein product, Tat, as a vaccine candidate. Being a very early regulatory protein and playing a major role in HIV-1 replication and pathogenesis, Tat represents an optimal candidate for vaccine development (Ensoli, 1990, 1993 and 1994; Chang, 1997). Tat is a key viral regulatory protein produced very early after infection, even prior to HIV integration, and is necessary for viral gene expression (Arya, 1985; Fisher, 1986; Ensoli, 1993; Wu, 2001), as well as cell-to-cell virus transmission and disease progression. In fact, in the absence of Tat, no or negligible amounts of structural proteins are expressed and, therefore, no infectious virus is made. Further, Tat is released by the infected T lymphocytes in the extra-cellular milieu (Ensoli, 1990 and 1993; Chang, 1997) and enters both infected cells, where it promotes HIV-1 replication, and uninfected cells, where it causes activation or repression of cytokines and cellular genes controlling the cell cycle (Frankel and Pabo, 1988; Ensoli, 1993; Chang, 1995). This approach is aimed at inducing both antibodies neutralizing extracellular Tat and T cell responses against virus-infected cells.

Several studies suggest that an immune response to Tat has a protective role and may control the progression of the disease in vivo (Reiss, 1990; Rodman, 1993; Re, 1995; Zagury, 1998; Re, 2001). In particular, a higher prevalence of anti-Tat antibodies has been shown in asymptomatic HIV-infected individuals as compared to patients in advanced stages of the disease (Krone 1988, Demirhan 2000, Re 2001) and in non-progressors as compared to fast progressors (Zagury 1998). We recently performed a cross-sectional and longitudinal study in a cohort of 252 individuals with accurately estimated dates of seroconversion and a median follow-up of 7.2 years (Rezza, in press). The results of this study revealed a strong association between the presence of anti-Tat antibodies and a slower progression to the disease. In fact, the risk of developing AIDS or severe immunodeficiency was 60% lower for anti-Tat positive individuals than for anti-Tat negative individuals. The longitudinal analysis also indicated that individuals who are persistently anti-Tat positive have the lowest risk of disease progression, whereas those who are persistently anti-Tat negative have the highest risk of developing severe immunodeficiency. Notably, individuals who are transiently anti-Tat positive/negative have a nearly 70% lower risk as compared to those who are persistently negative, providing evidence that the presence of anti-Tat antibodies is predictive of slower disease progression (Rezza, in press).

The immunogenic regions of Tat are conserved (both B and T cell) across all epitope M subtypes (Myers, 1995). Our recent data, in fact, indicate an effective cross-recognition of Glade B strain-derived (BH-10) Tat protein from the HTLVIIIB lab-adapted virus strain (Butte, 2003), which was isolated about 20 years ago (Ratner, 1985) by individuals infected by viruses circulating in Africa and belonging to different HIV-1 clades, thereby reflecting the high degree of conservation of the corresponding Tat regions. Specifically, sera from Italian, Ugandan and South African patients who were mainly infected with A, B, C and D and to a lesser extent, F and G HIV-1 subtypes, recognised the BH-10 Tat protein at similar levels (i.e. prevalence and titres of anti-Tat antibodies). This observation is reinforced by the results of sequence conservation analysis, demonstrating that the predicted amino acid sequence of Tat is well conserved among the different circulating viruses belonging to distinct HIV-1 clades and presents a relatively high degree of homology with the BH-10 Tat sequence (Buttò, 2003).

Homology is specifically high in the first exon-encoded portion of Tat, and, particularly, in the 1-58 region, which contains the functional domains of Tat and most of the B, T-helper and CTL epitopes so far identified (Buttò, 2003). Furthermore, epitope mapping studies of the Tat-positive sera from Italian, Ugandan and South African patients using linear peptides from the same BH-10 Tat sequence indicate the same pattern of recognition and confirm that the amino terminal region contains the major B cell epitope of Tat, although a large portion of anti-Tat antibodies is represented by conformational antibodies, independently from the infecting virus strain (Buttò, 2003). These findings indicate that the overall identity of Tat is preserved also at the conformational level and provide strong formal evidence that a Tat-based vaccine may indeed represent a "universal" tool against HIV, since it is capable of inducing a broad immune response that is effective against different virus clades.

We have confirmed this hypothesis through preclinical studies performed in different animal models, including mice and cynomolgus monkeys, which demonstrated that vaccination with a biologically active Tat protein or tat DNA is safe, elicits a broad and specific immune response and, most importantly, induces a long-term protection in vaccinated monkeys against infection with a highly pathogenic virus (SHIV 89.6P), which causes AIDS and death in these monkeys (Cafaro, 1999, 2000 and 2001).

In particular, the native Tat protein induced Th-1 and CD8+ CTLs cellular immune responses and high titres of anti-Tat antibodies and blocked primary infection with the simian/human immunodeficiency virus (SHIV) 89.6P, as indicated by maintenance of the CD4+ T cell counts and lack of disease onset in cynomolgus monkeys (Cafaro, 1999, 2000 and 2001). Of note, protection was prolonged, since no signs of virus replication were found, either in peripheral blood mononuclear cells, or in lymph nodes of the protected animals, during the 2 years of follow up. Further, no residual virus hidden in resting cells was detected in any of the protected macaques either in the plasma or in lymph nodes, upon two boosts with tetanus toxoid, a stimulus known to activate virus replication. Long-term protection correlated with the presence of high and stable humoral and cellular (CD4 and CD8 T-cell responses) against Tat (Maggiorella 2004). Finally, a pilot study conducted in SHIV infected macaques indicated that vaccination with either Tat DNA or protein is safe also in monkeys with AIDS.

In addition to representing a valuable antigen for a HIV/AIDS vaccine, biologically active Tat also displays immunomodulatory features that make it an attractive adjuvant for other antigens. In fact, we have recently shown that monocyte-derived dendritic cells (MDDC), and to a much lesser extent macrophages, but not B lymphoblastoid cell lines or T cell blasts, efficiently and rapidly take up native but not oxidised-inactive Tat (Fanales-Belasio, 2002). Upon uptake, native Tat promotes MDDC maturation and activation (increased expression of MHC antigens and co-stimulatory molecules, production of Th-1 cytokines and chemokines), leading to a more efficient presentation of both allogeneic and exogenous soluble antigens (Fanales-Belasio, 2002). Very recent data indicate that these effects are all mediated by the induction of TNFα expression by native Tat (Fanales-Belasio, submitted).

Further, we have shown that Tat modifies the catalytic subunit composition of immunoproteasomes in B and T cells either expressing Tat or treated with exogenous biological active Tat protein. In particular, Tat up-regulates latent membrane protein 7 and multicatalytic endopeptidase complex like-1 subunits and down-modulates the latent membrane protein 2 subunit. These changes correlate with the increase of all three major proteolytic activities of the proteasome and result in a more efficient generation and presentation of subdominant MHC-1-binding CTL epitopes of heterologous antigens (Gavioli, 2004). Thus, the modifications of antigen processing and of the generation of CTL epitopes by Tat may have an impact on both the control of virally infected cells during HIV-1 infection and the use of Tat for vaccination strategies.

In conclusion, there is a growing body of evidence that indicates that biologically active Tat functions as both an antigen and a potent adjuvant since i) it induces MDDCs maturation and activation toward a Th1 inducing phenotype, ii) it gains access to the major histocompatibility complex (MHC) class I pathway of presentation (Moy et al., Mol Biotechnol, 1996; Kim et al., J Immunol 1997), and iii) it modulates the proteasome catalytic subunit composition, modifying the hierarchy of the CTL epitopes presented in favour of subdominant and cryptic epitopes. Taken together these features make Tat an optimal candidate for an HIV vaccine, alone or in combination with other antigens.

In seropositive patients, this should contribute to reducing HIV-1 replication and disease progression. In individuals exposed to the virus after vaccination the vaccine could modify the virus-host dynamics at the very beginning of the infection and this would impact on the depletion of critical immune cells and the evolution of the infection, since the accumulating evidence indicates that the level of viral load at the beginning of the infection is a strong indicator of progression to disease (Mellors, 1996; Watson, 1997; Lifson, 1997; Ten Haaft, 1998; Staprans, 1999).

This approach also has the advantage that HIV components, which would show up in current tests for HIV, are not used, and patients test HIV-negative.

It is essential that the biologically active form of Tat is used, since the preservation of the native conformation permits: the induction of an effective Th1 cellular immune response; the induction of antibodies directed against conformational epitopes; and is necessary for the retention of Tat's adjuvant properties.

The Tat protein of HIV-1 (HTLV-IIIB strain, clone BH-10) is a molecule of 86 amino acids encoded by two exons. The product of the first exon is sufficient for the transactivation of the HIV-1 promoter. This region contains four domains including the amino terminal domain (aa 1-21), the cystein-rich domain (aa 22-37), the core (aa 38-48) and the basic domain (49-57). The cystein-rich region is necessary for zinc ion-mediated dimer formation and represents the transactivation domain. The basic region, rich in lysine and arginine residues, is required for nuclear localisation and can bind specifically to its RNA target, the transactivation response element (TAR) in the LTR (Hauber, 1989; Ruben, 1989; Roy, 1990; Chang, 1995). The C-terminal 14 amino acids of Tat that are encoded by exon 2 is not necessary for HIV-1 LTR transactivation but contains the arginine-glycine-aspartate (RGD) sequence which is a motif present in extracellular matrix proteins (Barillari, 1993; Brake, 1990). This region and the basic domain are required for the interaction of extracellular Tat with heparan sulphate proteoglycans and with cell surface molecules of the integrin family, respectively, and mediate uptake of Tat by dendritic cells (DC) (Fanales-Belasio, 2002).

In fact, biologically active Tat is selectively and efficiently taken up and processed by monocyte-derived DC, inducing their maturation and promoting their capacity to present, antigens, eliciting immune responses toward a Th1 pattern, and increasing T cell responses to other antigens. These functions are exerted only by the biologically active Tat protein and are abolished or greatly hampered after oxidation/inactivation of the protein (Fanales-Belasio, 2002).

Attempted production of Tat by conventional culture of recombinant hosts has been found to yield only biologically inactive Tat and is, thus, useless for the production of Tat on a commercial scale, as recovery of the biological properties is possible only after total denaturation and proper refolding of the product. Denaturation and refolding methods require the use of solvents not permitted in biologics intended for human use, so that these methods are neither useful nor can they serve as a guide for the production of biologically active Tat.

SUMMARY OF THE INVENTION

The invention provides methods for producing biologically active Tat, derivatives thereof, and precursors thereof. The methods comprise the step of culturing a host organism capable of expressing Tat when induced, wherein the expression of Tat is induced during the logarithmic growth phase of the host organism.

BRIEF DESCRIPTION OF THE DRAWINGS

FIG. 3 shows the pET-3c cloning expression region.
FIG. 4 shows the original sequence contained in the pCV-Tat vector excised with Eco RI cloned in the pET-3C.
FIG. 5 shows the cloning of 261 by of Tat gene.
FIG. 6 shows the insertion of tat in the pET-3c vector, with the CDS of ntd positions 22-282 highlighted.

DETAILED DESCRPTION OF THE INVENTION

Figure 1:
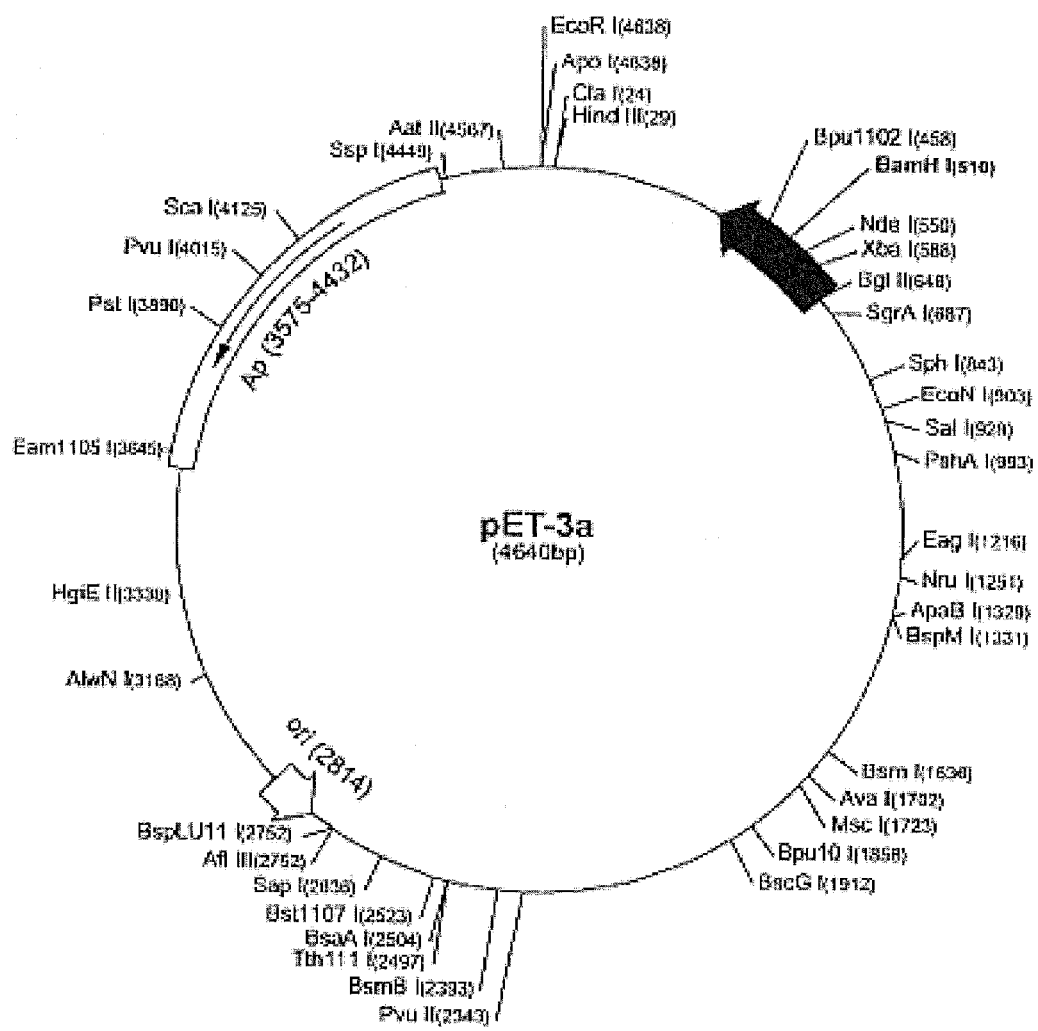
FIG. 1 shows the pET-3c vector.

Surprisingly, it has now been found that it is possible to produce biologically active Tat by inducing Tat production during the logarithmic growth phase of a recombinant, Tat-producing culture.

Thus, in a first aspect, the present invention provides a process for the preparation of biologically active Tat, comprising culturing a host organism capable of expressing Tat when induced, and wherein expression of Tat is induced during the logarithmic growth phase of the host organism.

Appropriate host organisms are preferably those which are readily susceptible of bulk culture under commercial conditions. Thus, it is preferred to avoid intricate process steps, where possible.

Preferred organisms are generally eukaryotic organisms, including bacteria and yeast. Any organisms capable of being transformed to express Tat may be employed. Examples include *Saccharomyces cerevisiae* (herein after "*S. cerevisiae*"), *Bacillus subtilis* (herein after "*B. subtilis*"), and *Escherrichia coli* (herein after "*E. coli*"). Particularly preferred is *E. coli*. The BL21 strains of *E. coli*, which have been specifically developed for bulk production, are preferred.

Biologically active Tat is generally monomeric, and is not oxidised, i.e. it is in its reduced form. For the purposes of cell cultivation, oxidation is unlikely, and induction during late growth phase leads to the production of dimeric, tetrameric, and/or multimeric Tat. It is not possible to obtain the biologically active, monomeric form of Tat from such molecules without treatment that would make the resulting Tat unusable in therapeutic formulations.

Thus, in an alternative aspect, the present invention provides a process for the production of monomeric Tat, comprising culturing a host organism capable of expressing Tat when induced, and wherein expression of Tat is induced during the logarithmic growth phase of the host organism.

The biological activity of the recombinant Tat protein can be evaluated using several tests, such as the uptake by monocyte-derived dendritic cells (MDDC), the rescue of a Tat-defective provirus, the transactivation of the HIV-1 LTR, the proliferation, migration and invasion of Kaposi's sarcoma cells and cytokine-activated endothelial cells (Ensoli, 1992 and 1993; Barillari 1993 and 1999; Fiorelli, 1995; Fanales-Belasio, 2002). However, due to excellent reproducibility and sensitivity, as well as its key role for vaccine efficacy, uptake by MDDC is the preferred potency test for recombinant Tat protein. Extracellular Tat is taken up by cells (Frankel and Pabo, 1988; Ensoli 1993; Chang 1997; Tyagi 2001), and, unlike most soluble proteins, enters the MHC class I presentation pathway and elicits CTL activity (Moy 1996; Kim 1997). It has been shown that MDDCs, among the most potent APCs, take up Tat much more efficiently than other cell types such as T cell blasts and B-lymphoblastoid cell lines and in a time-, dose- and maturation-dependent fashion (Fanales-Belasio 2002). Tat is taken up by MDDCs at doses as low as 0.01 ng/ml and the uptake peaks after 5-10 min. This process is markedly hampered by the oxidation/inactivation of the protein, and by low temperature (Fanales-Belasio 2002) and is used to characterise whether a specific Tat sample is biologically active, or not, herein.

Biologically active Tat is generally capable of inducing an immunological response in a non-immune compromised patient, and will have other characteristics as described hereinabove for biologically active Tat. A particularly preferred marker for biologically active Tat is its ability to be taken up by monocyte derived dendritic cells. A suitable test for Tat uptake by MDDC is described by Fanales-Belasio E, Moretti S, Nappi F, Barillari G, Micheletti F, Cafaro A, and Ensoli B. "Native HIV-1 Tat Protein Targets Monocyte-Derived Dendritic Cells And Enhances Their Maturation, Function And Antigen-Specific T Cell Responses" in J. Immunol. 2002, 168:197-206.

Thus, in one aspect, the present invention provides a process for the preparation of biologically active Tat, comprising culturing a host organism capable of expressing Tat when induced, and wherein expression of Tat is induced during the logarithmic growth phase of the host organism, wherein the measure of biological activity is the ability of the Tat to be taken up by monocyte derived dendritic cells.

Indeed, in all aspects of the invention, the measure of biological activity may be the ability of the Tat to be taken up by monocyte derived dendritic cells.

Any variant or mutant of Tat that exhibits the desired properties of Tat, particularly the ability to be taken up by MDDC, may be produced in accordance with the present invention, and is included within the definition of "biologically active Tat". Such variants and mutants may be obtained naturally, such as from any strain, or clade, of HIV, or may be obtained by genetic manipulation of nucleic acid encoding Tat. Such manipulation may be by deletion, insertion or inversion, including combinations thereof, provided that the properties of biologically active Tat are retained. In particular, it is preferred to retain those areas identified hereinabove as being conserved across clades. Lead sequences and/or tail sequences may be incorporated, for example, in order to assist secretion and/or provide a level of protection against digestion, for example. The Tat coding sequence may comprise the two naturally occurring exons, with or without the intervening intron, and need only contain sufficient sequence information to retain biological activity. It is generally preferred, however, to use as much of a naturally occurring sequence as possible.

Tat is well known in the art. However, it is preferred that the tat protein is that shown in SEQ ID NOs. 2 or 3, especially after any post translational modification (such as cleavage of the N' term Met). The same follows for Tat shown in SEQ ID NO.s 5 and 6. Where mutants or variants are tat are required, as is preferred, these will have biological activity and preferably that are at least comparable with "biologically active tat." Such mutants or variants will preferably have at least 70%, more preferably at least 75%, more preferably at least 80%, more preferably at least 85%, more preferably at least 90%, more preferably at least 95%, more preferably at least 99%, more preferably at least 99.5%, and most preferably at least 99.9% sequence homology, as appropriate, to the amino acid sequences shown in said SEQ ID NOs, at least the nucleotide sequences shown therein as encoding the amino acid sequence of tat, or the full nucleotide sequences shown therein. Thus, it is particularly preferred that Tat is that shown in SEQ ID NOs. 2, 3 5 or 6, or a mutant or variant thereof having biological activity and at least 70% sequence homology, said sequences. The higher levels of sequence homology mentioned above are also preferred in this instance.

Any nucleic acid sequence, such as is described above, may be used to encode Tat, but it is preferred that the expression product obtained from the cultured host is identical with, or substantially identical with, Tat that has been shown in the art to be biologically active and to have desired properties.

The host organism may be transformed genomically, or by incorporation of a suitable expression plasmid. In order to be inducible, it is preferred that the Tat-encoding sequence be under the control of an inducible promoter. By "inducible promoter" is meant a promoter that is not constitutive and which only leads to expression of the coding sequence under its control under selected circumstances.

Inducible promoters generally fall into two categories, the first category being that in which the polymerase is generally constitutively present, but will not recognise the promoter, or will only recognise it to a limited extent, in the absence of a facilitating ligand. The second category is that in which the promoter is only recognised by a specific polymerase which, itself, is not constitutively expressed and may be under the control of an inducible promoter.

In the BL21 strains of *E. coli*, T7 RNA polymerase is under the control of a lac (IPTG inducible) promoter, so that production of this polymerase can readily be induced by the addition of IPTG. All that is necessary for the control of an exogenous sequence, then, is for that sequence to be associated with the T7 promoter. Addition of IPTG to a culture of BL21 *E. coli* will stimulate production of T7 RNA polymerase which can then transcribe the sequence under the control of the T7 promoter. In the present invention, a Tat encoding sequence is under the control of the T7 promoter in this example.

The host organism may be cultured under any suitable conditions permissive of expression in a manner well known in the art for expression of exogenous protein. The only significant deviation from techniques well known in the art is that induction of the exogenous protein, Tat, is effected and terminated before the log phase begins to plateau. In conventional protein production cultures, the OD is generally allowed to reach 1.2 or higher before induction. While induction at this level yields similar quantities of Tat to that achieved in accordance with the present invention, the Tat is not biologically active. By inducing during log phase rather than when the log phase has begun to plateau significantly, it is possible to obtain a similar yield to that obtained at an OD of 1.2, but wherein the Tat is biologically active. Preferred OD's are in the range 0.4 to 0.9, more preferably 0.45 to 0.8, inclusive. Particularly preferred is an OD for induction of 0.5 to 0.7, inclusive, and an OD of about 6 has been found to provide excellent yields of biologically active Tat.

Tat produced by the process of the present invention is particularly advantageous in that it can be obtained without being contaminated by proteins of animal origin in the fermentation step. It is also an advantage that, as solvents are not permitted to be used in biologics for human, then the use of solvents is avoided. It is a further advantage that Tat produced in accordance with the present invention is able to be formulated to withstand storage at temperatures as low, or lower than, −80° C.

Tat obtained in accordance with the present invention can be used as desired. It is particularly preferred to use this Tat in vaccine formulations, as described in the art, but other uses for the thus produced Tat are envisaged and are equally within the ability of those skilled in the art.

In a further aspect, there is provided biologically active Tat as produced in accordance with a process of the present invention.

The present invention will now be described further by the following, non-limiting Examples. Any references cited herein are hereby incorporated by reference to the extent that they do not conflict with the present invention.

EXAMPLES

HIV-1 Tat Gene

The structure of the tat gene has been defined by molecular cloning and nucleotide sequencing of a trans-activation-competent cDNA, pCV-Tat (Ensoli, 1993). The Tat protein has been shown to be translated from a doubly spliced RNA containing two coding exons (Aldovini, 1986). The first coding exon (nucleotides 5411-5625) (Ratner, 1985), located immediately before the env gene and specifying 72 amino acids, has been shown to be necessary and sufficient for trans-activation (Sodroski, 1985; Seigel, 1986). The second coding exon codes for the additional 14 amino acids and is located between nucleotide 7956 and nucleotide 8001, bringing the total size of the Tat protein to 86 amino acids.

The tat gene used in this process was derived from the pCV-Tat plasmid (Ensoli, 1993). To generate the tat expression plasmid pCV-Tat (full length tat cDNA), primers from −61 to −41 and +270 to +289 of the tat cDNA were used for amplification by the polymerase chain reaction (PCR). The primers were designed with a Pst1 site at the 5' end as a linker. PCR amplified fragments were then digested with Pst1 and cloned into the Pst1 site of pCV0. The sequence and the orientation of the constructs were verified by nucleotide-sequence analysis. The tat gene, originally derived from HTLV-III-infected cell lines, was later identified as derived from the HTLV-IIIB isolate, BH-10 clone (clade B).

Expression System

The pET System is a powerful system for the cloning and expression of recombinant proteins in *E. coli*. Based on the T7 promoter-driven system originally developed by Studier and colleagues (Studier, 1986 and 1990; Rosenberg, 1987), Novagen's pET System has been used to express thousands of different proteins. The pET System provides vector-host combinations that enable tuning of basal expression levels to optimise target gene expression (Rosenberg, 1987). After plasmids are established in a non-expression host, they are most often transformed into a host bearing the T7 RNA polymerase gene (λDE3 lysogen) for expression of target proteins. In λDE3 lysogens, the T7 RNA polymerase gene is under the control of the lacUV5 promoter. This allows some degree of transcription in the uninduced state. For more stringent control, a host carrying pLysS can be used. The pLys plasmids encode T7 lysozyme, which is a natural inhibitor of T7 RNA polymerase, and thus reduces its ability to transcribe target genes in uninduced cells.

For the expression of recombinant Tat, bacterial strain BL21(DE3) was transformed with a pET-TAT and pLysS plasmids. The BL21 cells are the most widely used hosts. These cells are deficient in the ion protease and lack the ompT outer membrane protease (Table 1). BL21 cells are sensitive to rifampicin, pLyS express T7 lysozyme, which suppresses basal T7 RNA polymerase.

TABLE 1

Characterisation of the bacterial strain used for the expression of the Tat protein
BACTERIAL STRAIN BL21(DE3)pLysS

| Strain Genotype: | F⁻ ompT hsdS$_B$ (r⁻m⁻) gal dcm (DE3) pLysS (Cm$^R$) |
|---|---|
| Bacterial Strain genetic markers: | F⁻ = does not contain the F episome<br>ompT = Lacks an outer membrane protease<br>hsdS = Abolishes both restriction and methylation of DNA at certain sites (r⁻m⁻)<br>gal = Unable to utilise galactose<br>dcm = No methylation of cytosines in the sequence CCWGG<br>Cm$^R$ = resistance to chloramphenicol |

The pET vectors derive from pBR322, and are the precursors to many pET family vectors. The pET-3a-d vectors carry an N-terminal T7 Tag sequence and BamHI cloning site. The pET-3c vector has been used in this study (FIG. 1). The sequence of the pET-3c vector is provided in the sequence listing as SEQ ID NO. 7.

The map for pET-3c is the same as pET-3a (shown) with the following exceptions: pET-3c is a 4638 bp plasmid, subtract 2 bp from each site beyond BamH I at 510; an Nco site is substituted for the Nde I site with a net by deletion at position 550 of pET-3c.

Figure 2:
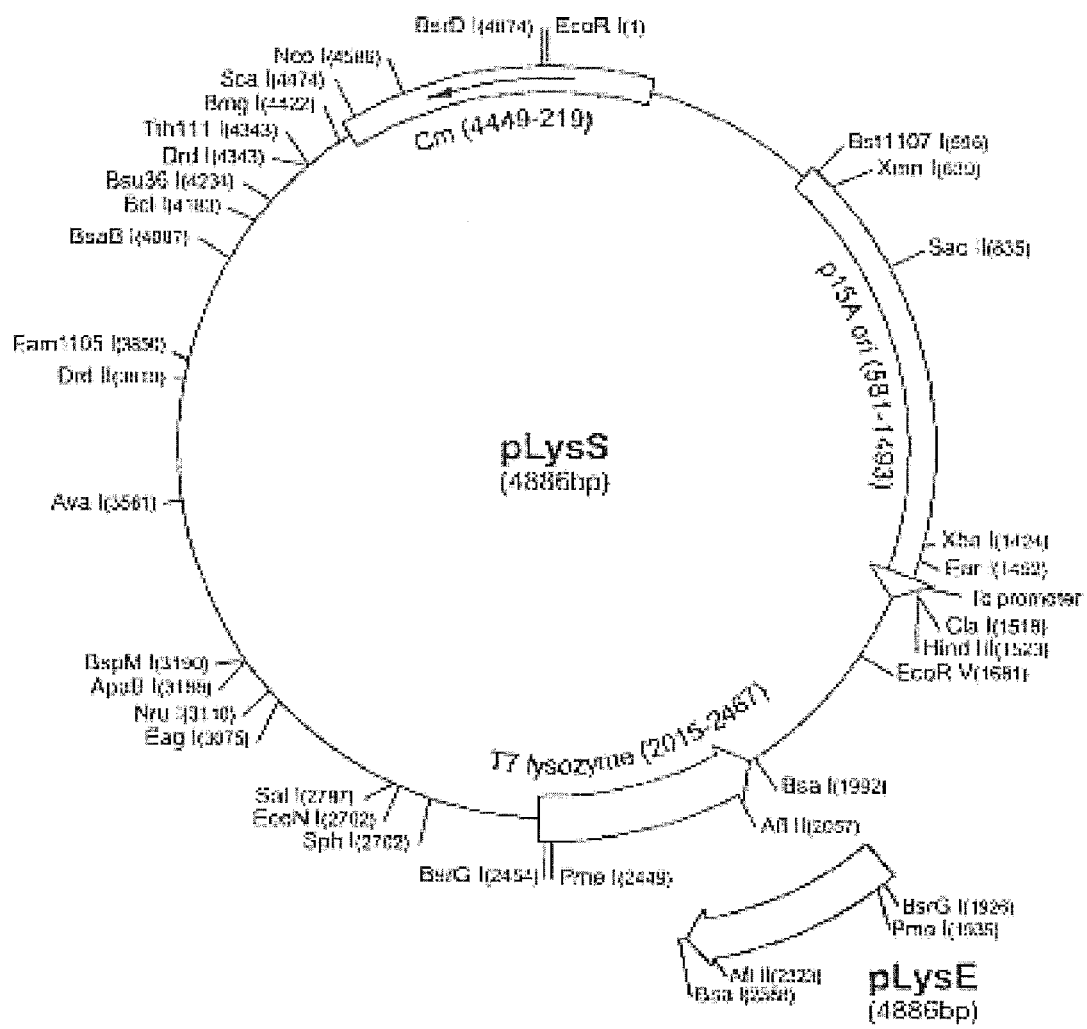
FIG. 2 shows the pLysS plasmid.

The plasmid pLysS is a 4886 bp plasmid constructed by insertion of the T7 lysozyme gene into the BamHI site of pACYC184 (Studier, 1986 and 1990). This plasmid is not a cloning vector, and is used in λDE3 lysogenic hosts to suppress basal expression from the T7 promoter by producing T7 lysozyme, a natural inhibitor of T7 RNA polymerase (FIG. 2). The sequence of the pLyS vector is provided in SEQ ID NO. 8.

Construction of the Expression Vector and Preparation of the Product Cell Line pET-TAT was constructed by cloning the 261 bp Tat from the pCV-Tat expression plasmid into the 5' NdeI and 3' BamH1 sites of pET-3c (FIG. 3 and SEQ ID NO. 1, which show the pET-3c cloning expression region).

The 261 bp fragment of the tat gene was amplified from the pCV-TAT plasmid using a 5' primer containing the NdeI cleavage site and a 3' primer containing the BamH1 cleavage site (FIG. 4, which shows the original sequence contained in the pCV-Tat vector excised with Eco RI cloned in the pET-3C: also shown in SEQ ID NOS. 2 and 3).

Both the amplified tat product and the pET-3c vector were digested with NdeI and BamH1. Digestion was then followed by a ligase reaction, transformation into the NovaBlue bacterial strain and selection of tat positive clones by PCR screening (FIG. 5, which shows the cloning of 261 bp of Tat gene, as also shown in SEQ ID NO. 4.).

The correct insertion of tat cDNA in the pET-3c vector was sequenced by the Sanger method with the ABI PRISM BigDye Terminator Cycle Sequencing Kit (Applied Biosystems) using the T7 promoter and T7 terminator as sequencing primers (FIG. 6, which shows the insertion of tat in the pET-3c vector, with the CDS of ntd positions 22-282 highlighted, as also shown in SEQ ID NOS. 5 and 6).

The recombinant plasmid obtained (pET-3c/Tat) was used to transform various *E. coli* strains containing the gene coding for the T7 RNA polymerase under the control of IPTG (isopropyl-(3-D-thiogalactopyranoside)-inducible lacUV5 promoter. Efficacy of the plasmid construct and the selection of the best bacterial strain were obtained evaluating, by SDS-PAGE, the production of recombinant Tat protein after induction of bacterial cultures. For the expression of pET-3C/Tat in BL21 (DE3) pLysS, overnight cell cultures were diluted 1:10 in synthetic medium (pH 7.5) containing; ampicillin 1 ml/L (stock solution 25 mg/mL), chloramphenicol 1 ml/L (stock solution 34 mg/mL), thiamin 0.5 mL (stock solution 4.5 mg/mL), Mg solution 1.25 ml/L (stock solution 240 mg/mL), and, glucose 12 ml/L (stock solution 630 mg/mL).

Diluted bacteria were then incubated at 37° C., up to 0.6-0.7 optical density at 600 nm. In order to optimise expression conditions of the recombinant protein several induction experiments were performed. The most efficient Tat production was obtained by adding 1 mM IPTG to the culture for 4 hours at 37° C. At the end the bacteria were centrifuged and pellets resuspended in lysis buffer. The bacterial lysates containing the Tat protein were sonicated and centrifuged in order to solubilise the protein. The pellets were then resuspended in a buffer containing mannitol, glycerol, phosphate buffer, DTT and NaCl. The samples were sonicated again and centrifuged at 10,500×g for 30 minutes, supernatants filtered and loaded onto a DEAE SEPHAROSE FAST FLOW (Amersham Pharmacia Biotech, Uppsala, Sweden) column. The protein was then eluted with 1 M NaCl. Tat-containing fractions were collected and diluted 1:1 vol. and loaded onto heparin sepharose CL-6B (Amersham Pharmacia Biotech, Uppsala, Sweden) column. The protein was then eluted with 2M of NaCl. Tat-containing fractions were collected and dialysed in order to remove NaCl. The purity grade of the protein obtained by the above procedure was verified by SDS-PAGE. The yield of protein recovered is indicated in Table 2.

TABLE 2

Purification of Tat protein expressed in *E. coli*

| Cell-free extract | Total recovery from 1 litre of bacterial culture |
|---|---|
| pET-3C BL 21 (DE3) pLysS | 4-5 mg |

Figure 7:
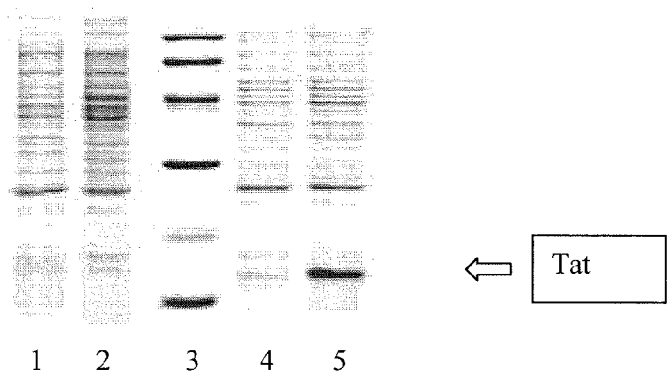
FIG. 7 shows the protein band corresponding to recombinant Tat. Lane 1=Uninduced (under standard conditions); Lane 2=Induced (under standard conditions); Lane 3=LMW; Lane 4=Uninduced (after optimisation); and Lane 5=Induced (after optimisation).

Several parameters were optimised in accordance with standard practice, including:
 IPTG concentration during induction
 Co-transfection with the pLysS plasmid to suppress basal expression by the T7 promoter
 Oxygen, temperature and biomass production The result of this work is immediately evident by the appearance of the protein band corresponding to recombinant Tat. See for instance FIG. 7, where:
Lane 1=Uninduced (under standard conditions)
Lane 2.=Induced (under standard conditions)
Lane 3.=LMW
Lane 4.=Uninduced (after optimisation)
Lane 5.=Induced (after optimisation)

Under defined optimal conditions we were able to induce expression in the above transformed *E. coli* of 4 to 5 mg of recombinant Tat. Unfortunately these conditions did not provide biologically active Tat.

Figure 8:
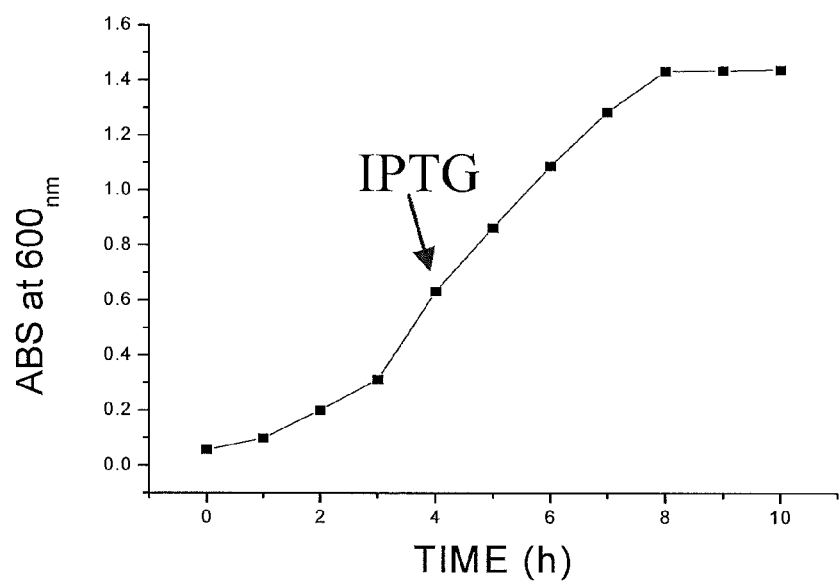
FIG. 8 shows that the optimum OD of the cell culture was found to be 0.5 to 0.7 O.D. units, preferably 0.6 O.D.

Instead, by chance, it was found that biologically active recombinant Tat can be obtained, provided that *E. coli* is present at a defined concentration at the time of IPTG addition and until the end of the induction time. The optimum OD of the cell culture was found to be 0.5 to 0.7 O.D. units, preferably 0.6 O.D. units at the time of IPTG addition. This behaviour in the expression of Tat is completely unexpected. The O.D. at which a culture is conventionally induced is that at which the greatest biomass can be harvested. There is no known reason why adherence to conventional wisdom yields biologically inactive Tat, while expression during mid log phase yields biologically active Tat. This result is extremely surprising. This is shown in FIG. 8, which is a description of the conditions that permits the recovery of biologically active recombinant Tat.

Figure 9:
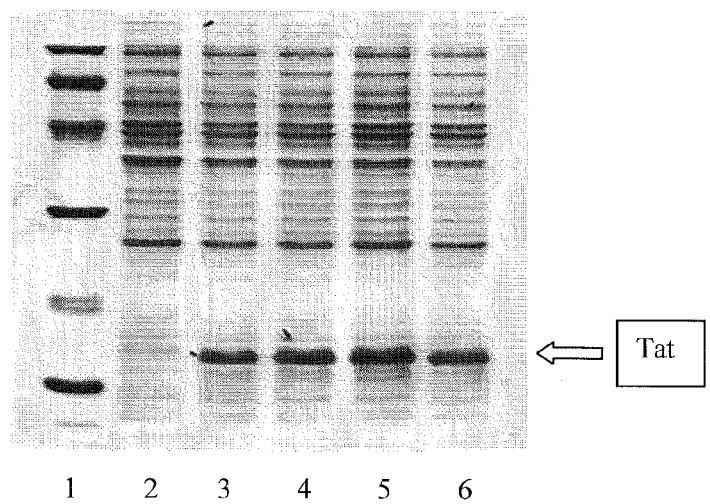
FIG. 9 shows that the amount of soluble Tat recovered after induction at high OD's is similar to that recovered after induction at low OD's, but is not biologically active. Lane 1=LMW; Lane 2=Uninduced; Lane 3=Induced at 0.6 OD (1 hour); Lane 4=Induced at 0.6 OD (2 hours); Lane 5=Induced at 0.6 OD (3 hours); Lane 6=Induced at 1.2 OD (2 hours).

It is known to modify temperature and harvesting conditions to prevent the precipitation of expressed recombinant protein in inclusion bodies, and this occasionally requires induction at OD or temperature values lower than the maximum potentially obtainable. The case with Tat differs, as the amount of soluble Tat recovered after induction at high OD's is similar to that recovered after induction at low OD's, but is not biologically active. See for instance FIG. 9, where lane:
 1.=LMW
 2.=Uninduced
 3.=Induced at 0.6 OD (1 hour)
 4.=Induced at 0.6 OD (2 hours)
 5.=Induced at 0.6 OD (3 hours)
 6.=Induced at 1.2 OD (2 hours)

Figure 10:
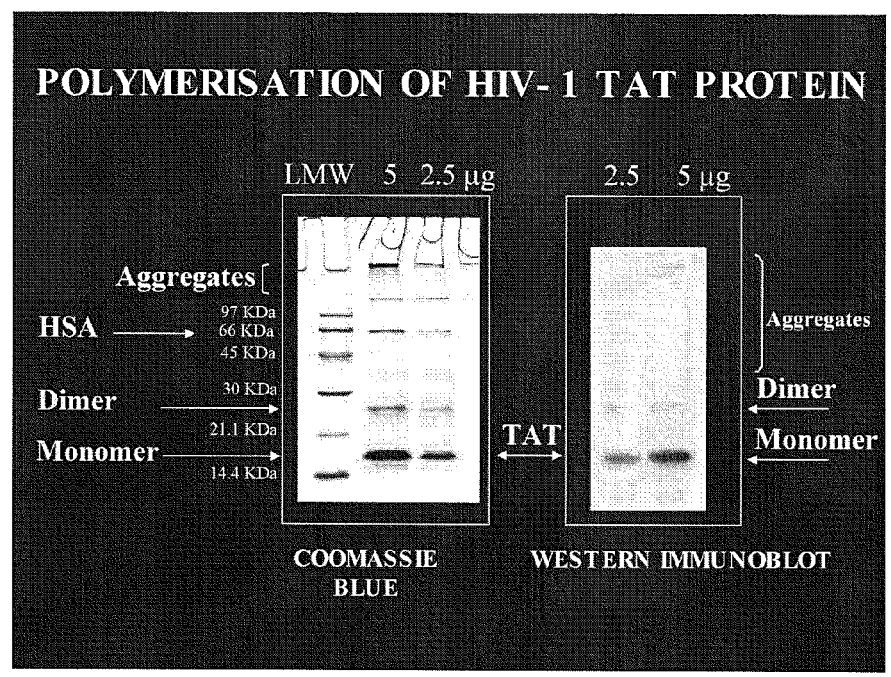
FIG. 10 shows Tat protein without biological activity but recovered in soluble form.

The loss of biological activity of recombinant Tat is not connected with its expression as a soluble protein or as a recombinant protein within inclusion bodies but, rather, is related to recovery as a monomer. Recombinant protein that is present in multimeric form, and which is non-dissociable under standard SDS-PAGE conditions, does not show biological activity. FIG. 10 shows Tat protein without biological activity but recovered in soluble form.

Method of Preparation of the *E. Coli* Master Cell Bank (MCB) for the Production of HIV-1 Recombinant Tat Protein (*E. Coli* BL21 DE3 pLysS MCB)

The MCB is defined as an aliquot of a single pool of cells, which generally has been prepared from a selected cell clone under defined conditions, dispensed into multiple containers, and stored under defined conditions.

Vegetable peptone agar plates were prepared to isolate a single colony of *E. coli* BL21(DE3) transformed with pET-TAT and pLysS plasmid. Liquid media containing vegetable peptone, dextrose, di-potassium hydrogenphosphate, yeast extract and sodium chloride, were prepared and, just before autoclaving, agar tablets were added. Sterilisation was performed by autoclaving for 20 min at 121° C. The medium removed from the autoclave was gently swirled to distribute the agar evenly throughout the solution. The medium was allowed to cool to 30-37° C. before adding antibiotics (50 µg/mL ampicillin and 34 µg/mL chloramphenicol). Plates were then poured directly from the flask, allowing 20 mL of vegetable peptone agar per 90 mm plate. When the medium had hardened completely, the plates were inverted and stored at 4° C. until needed. The plates were then removed from storage 1-2 hours before they were used.

One mL of the *E. coli* BL21(DE3) pLysS vial (directly from a frozen glycerol stock) was aseptically transferred into 9 mL of PBS and agitated to mix. This step was repeated preparing log dilutions of the bacteria up to and including $10^{-10}$. The cover from a vegetable peptone agar plate was removed and 200 µL of the $10^{-1}$ dilution added to the plates. This step was repeated for each dilution. The dilutions were spread over the surface of the vegetable peptone agar plates, ensuring that the plates were completely dry and replacing the cover. Incubation was performed aerobically at 37° C. for a minimum of 24 hours. After this time of incubation the inoculated vegetable peptone agar plates were examined for single bacterial colonies.

A single colony (from the highest dilution possible) of *E. coli* BL21(DE3) transformed with pET-TAT and pLysS plasmid, was inoculated into a Vegetable Peptone Broth (vegetable peptone, dextrose, di-potassium hydrogenphosphate, yeast extract and sodium chloride) containing 50 µg/mL ampicillin and 34 µg/mL chloramphenicol and then incubated aerobically for 5 hours at 37° C. in the incubator shaker set at 200 rpm. The culture was checked visually at hourly intervals until the culture started to become cloudy. The optical density of the sample was measured at 600 nm. Vegetable peptone broth was used as a zero before each reading. Incubation was performed until the optical density reached the range of 0.4 to 0.6. When the optical density reached this range, 30% of glycerine (under sterile condition) was added to the cell suspension, the suspension swirled for approximately 30 seconds for mixing and then 1 mL of the mix transferred in 2 mL cryotubes (2 mL Nalgene cryotubes). The cryotubes were filled in numerical order. The vials of the MCB were stored at −80° C. The master cell bank was further characterised by standard biochemical and molecular methods.

Manufacture of Recombinant Tat Protein Performed for the Three Validation Batches The Production Process has been Implemented and Performed at AVITECH Antigen Production Unit (Diatheva s.r.l GMP facility) Fano-Italy 1) Fermentation and Harvesting 1.1 *E. Coli* BL21 DE3 pLysS Starter Culture The vegetable peptone broth plus 50 µg/mL Ampicillin and 34 µg/mL Chloramphenicol (VPB+AC), 8×2000 mL Erlenmeyer flasks were transferred into the laminar flow cabinet of the Fermentation suite, to prepare the *E. coli* BL21 DE3 pLysS starter culture. Four hundred ml of the VPB+AC were aseptically transferred into the sterile 2000 mL flasks. The Erlenmeyer flask was inoculated with 400 µL of a MCB *E. coli* suspension and labelled as the Starter Culture. The cultures were incubated aerobically at 37° C.±2° C. in the Innova incubator shaker set at 250 rpm. After 16 hours of incubation, a 5 mL sample was removed from the Erlenmeyer flasks by transferring the flask into the laminar flow cabinet of the Production suite, and aseptically removing the required volume with a 10 mL pipette. The sample was transferred into sterile 50 mL centrifuge tubes. The optical density of the sample was measured at 600 nm using the Spectrophotometer and the measurement recorded. An appropriate dilution of the sample was made in VPB+AC, so that the optical density of the dilution falled between 0.3-0.7. The VPB+AC was used as zero before each reading. The sampling and measurement were repeated every hour, and more frequently as the optical density reading approached the target of 2.0. When the optical density was above 2.0, the cultures were transferred into 2 L sterile PIREX bottle. Label was attached to the sterile PIREX bottle containing culture. 395 mL starter culture was used for inoculation of the BIOSTAT C15. The raw material for the fermentation cell concentrate was transferred into the Fermentation suite.

1.2 Cell Culture and Harvest

The fermenter connectors and tubing sets were prepared, packaged and sterilised using cycle 1 of the Fedegari autoclave FMV. At the end of the cycle, the autoclave record was checked to ensure that the minimum sterilising conditions were met (load probe 121° C. for 15 minutes) and autoclave printout attached. The Biostat C15 fermenter was prepared for sterilisation. The pH probe calibrated, the pH probe calibration details and time recorded. Two settle plates were placed on the laboratory bench, the plates exposed and the time recorded. The fermenter basic media was prepared as follows: potassium dihydrogenorthophosphate, ammonium hydrogen phosphate, citric acid monohydrate were added to the Biostat C15 vessel; then purified water were added to the vessel, the agitation set to 100 rpm and control mode to PID. The solution was mixed to ensure that all the components had dissolved.

Afterwards, 1.512 gr of the Iron (III) citrate hydrate, 37.5 mg of Cobalt (II) chloride hexahydrate, 225 mg of Manganese (II) chloride tetrahydrate, 22.5 mg of Copper (II) chloride dihydrate, 45 mg of Boric Acid, 31.5 mg of Sodium molybdate dehydrate, 507 mg of Zinc acetate dihydrate and 221.5 mg of EDTA were added to the BIOSTAT C15. The settle plates were covered, the end time and total time recorded. The Biostat C 15 was prepared for sterilisation, the sterilisation temperature set to 122° C. and sterilisation time set to 20 minutes. The growth temperature was set to 37° C. and control mode to PID. After ensuring that the sample and inoculation connections were attached, the Biostat C 15 including the basic media were sterilised. The DO electrode was calibrated and the room cleaned. The sterile ammonia solution was transferred into the fermentation room and the appropriate sterile tubing connected. The ammonia solution was attached to the Biostat C15, pH set to 7.5 and control mode to PD. A 2-point calibration of the pH meter was performed. The pH of the sample was measured and the calibration zero adjusted as required. The antibiotic solutions (ampicillin, thiamine, magnesium, glucose, chloramphenicol) were transferred into the fermentation room and 15 mL of antibiotic solution Amp25, 7.5 ml of thiamine solution, 18.75 mL of magnesium solution, 500 mL of glucose solution and 15 mL of chloramphenicol solution were aseptically added to the Biostat C15. The Biostat C15 was inoculated with the *E. coli* BL21 DE3 pLysS starter culture as follows: the inoculation port was sterilised, agitation set to off and the starter culture tubing set attached to the inoculation connector tubing set and the tubing inserted into the pump head of the peristaltic pump. The port assembly was opened and the starter culture pumped into the vessel changing the bottles as required to inoculate the whole starter culture. The port assembly was closed and sterilised. The agitation was set to 100 rpm and the control mode changed to PID. The airflow was adjusted to 50 liters per minute, the DO set to 50 and control mode to PID. The agitation control mode was set to DO and the upper agitation set point to 400 rpm. The optical density of the sample was measured at 600 nm using the spectrophotometer (basic media was used as zero before each reading) and measurements recorded. At an optical density of at least 0.6, 15 mL of 1M IPTG (final concentration 1 mM) were added. The fermentation was continued for a maximum of 4 hours post IPTG induction, sampling hourly. After 4 hours post IPTG induction the temperature was set to off, pH loops set to off and the agitation set point changed to 100 rpm. The harvest assembly line and tubing was connected. Six rotor bottle are placed in the filling rack, and the liner is placed into each bottle. The liners are loaded with material through a funnel. This operation is performed under a laminar flow cabinet. The valve in the neck of each liner is then sealed and the liner necks folded to fit inside the bottle. The bottle are sealed with rotor plugs and cap/closure, and the sealed bottles are placed into rotor canisters for centrifugation. After centrifugation, the centrifuge bottles were transferred into the laminar flow cabinet and the liner valves cut off and the supernatant decanted. The liners were sealed for pellet storage at −20° C. Each liner containing the pellet were labelled were placed into a storage bag. The bag was placed into the refrigerator. The temperature of the immediate bag surroundings was measured using the Testo 175 T1 temperature datalogger and the printout included in the batch records.

2) Separation 2.1 *E. Coli* BL21 DE3 pLysS Cell Disruption

The lysis buffer was placed into the refrigerator to cool. The Microfluidiser was cleaned and prepared for cell disruption. The microfluidiser was cleaned prior to use. The reservoir was filled with 1M Sodium Hydroxide and the caustic processed through the system maintaining a pressure of at least 1000 BAR. The microfluidiser reservoir was filled with the 1 M Sodium Hydroxide. The sodium hydroxide was processed through the microfluidiser. The prime relief valve was opened and the motor turn on to purge any trapped air. The secondary pressure value was closed until 100 BAR ware reached, and the primary pressure value was closed until 1000 BAR were reached.

To prevent air entering the system, the reservoir was filled with 1M sodium hydroxide. A 3-point calibration of the pH-meter was performed. The pH of samples was measured and samples flushed with water for injection until the pH reached a level <7.5. The microfluidiser was flushed with 500 mL of 0.1M NaCl lysis buffer prior to introduce the sample. The microfluidiser was stopped before the reservoir totally empties to avoid trapping air. The *E. coli* BL21 DE3 pLysS cell pellet was removed from the refrigerator. The Testo 175 T1 temperature datalogger was stopped and printout retained. The cell paste was transferred into the laminar flow cabinet. The cell paste was resuspended 50 ml/liter of bacterial culture. 700 mL of cold 0.1M NaCl Lysis Buffer was added to the cell paste and gently mixed. The cell lysis solution was processed through the microfluidiser for one pass only at 680 BAR. The lysis suspension was poured into the reservoir. The intensifier pump started and the pressure control knob adjusted to increase pressure to approximately 680 BAR. The lysis suspension was processed through the microfluidiser. After the sample had been fully processed, 50 mL of 0.1N NaCl lysis buffer was added to the reservoir and processed through the system to ensure all the lysis suspension has been processed and passed out the product outlet. The microfluidiser was stopped once all the lysis buffer has been processed. The processed product was collected in centrifuge bottle and then pelleted at 8.000 rpm for 1 h at 4° C.

The supernatant was removed from each line and bulked into sterile PIREX bottles. The supernatant solution, sterile 1000 mL PIREX bottles, 0.45 µm filter and tubing set were transferred into the laminar Flow Cabinet. The filter was assembled as follows using aseptic procedures: a) the free end of the tubing was inserted into the supernatant solution; b) the other end of the tubing set was connected to the 0.45 µm filter; c) the filter was clamped into the stand; d) the tubing was inserted into the pump head of the dispensing pump. The cap from a 1 L PIREX bottle was removed and the bottle was placed under the filter.

The supernatant solution was filtered using the dispensing pump. When the 1 L PIREX bottle was filled, the cap was replaced. The bottles were removed from the Laminar flow Cabinet directly to the Cleanroom by using pass-box, for immediate purification.

3) Purification 3.1 Preparation for DEAE Chromatography

The AKTA was used to pack DEAE chromatography column and was cleaned. All lines were removed and placed in a 1M NaOH Nalgene PTFE container. In "System control", "Manual" was clicked, then "System wash", then "Insert" e finally "Execute" to progress with the clean of the system. After 30 minutes, the program was paused. In "System control", "Manual" was clicked, then "System wash", insert the "Folw rate" then "Execute" to progress with the clean of the outlet valves of the system. The sample valve was washed with 1M NaOH and with the same method. After 30 minutes the program was paused. The lines from 1M NaOH were removed and placed in water for injection until the pH reach 6-8 value. Then, the lines from water for injection were removed and placed in 5000 mL of 0.1M NaCl lysis buffer in a 5000 mL Nalgene PTFE container. "Continue" was clicked and the system was flushed with buffer. The waste container was emptied and a 20 L carboy bag was used as waste. Visual inspection of the chromatography columns was completed to ensure the resin was homogenised and no air bubbles were visible in the packed column. The inlet and outlet lines of the column were connected to the appropriate connections in the AKTA Explorer.

3.2 First Step of Tat Protein Purification

In the Unicorn software, "System control" was clicked and in the file menu was selected: "Run", then was selected the file "DEAE". Several Dialogues boxes appeared, asking for information about the run: Variables, Notes, Method information and Result. The lines was placed as follow: line A11 connected to the 0.1M NaCl lysis Buffer bag; line B1 connected to the 1 M NaCl lysis buffer bag; line S1 for the purified material. The F3 was connected to a 2 L sterile PIREX bottle for collection of the eluted product. The F4 was connected to a 10 L Nalgene PTFE container for collection of the load flowthrough and wash.

The F1 was connected to go to a waste 20 L Nalgene container. All the collection vessels were labelled appropriately. The program was ready to start. The method was programmed, any manual actions taken during the purification run was logged in the log record and stated in the "Comments". The target protein eluted at the 1M NaCl lysis buffer wash (Elution block). In the chromatogram window, an absorbance peak detected at a wavelength of 280 nm appeared at the same time as the conductivity increased. Collection was programmed and the method automatically finished. The DEAE elute was transferred from the 2 L sterile PIREX bottle using a clean cylinder into a sterile PIREX bottle in the laminar flow hood. The DEAE elute pool was diluted 1:1 with salt-free lysis buffer, giving a final concentration of 0.5M NaCl in the solution loaded onto the Heparin sepharose column.

3.3 Preparation for Heparin Sepharose Chromatography

The AKTA was used to pack DEAE chromatography column and was cleaned. All lines were removed and placed in a 0.5M NaOH Nalgene PTFE container. In "System control", "Manual" was clicked, then "System wash", then "Insert" e finally "Execute" to progress with the clean of the system. After 30 minutes, the program was paused. In "System control", "Manual" was clicked, then "System wash", insert the "Flow rate" then "Execute" to progress with the clean of the outlet valves of the system. The sample valve was washed with 0.5M NaOH and with the same method. After 30 minutes the program was paused. The lines from 0.5M NaOH were removed and placed in water for injection until the pH reach 6-8 value. The lines from water for injection were removed and placed in 10 L of 0.5M NaCl lysis buffer in a 10L Nalgene PTFE container. "Continue" was clicked and the system was flushed with buffer. The waste container was discarded and replaced with an empty container. Visual inspection of the chromatography column was completed to ensure the resin was homogenised and no air bubbles were visible in the packed column. The inlet and outlet lines of the column were connected to the appropriate connections in the AKTA Explorer and the details of these were recorded.

3.4 Second Step of Tat Protein Purification

In the Unicorn software, "system control" was clicked and in the file menu was selected: "Run", then was selected the file "Heparin". Several Dialogues boxes appeared, asking for information about the run: Variables, Chromatography, Notes, Method information and Result. The lines were placed as follow: line A11 connected to the 0.5M NaCl lysis Buffer bag; line B1 connected to the 2 M NaCl lysis buffer bag; line S1 for the purified material. The F3 was connected to a 2 L sterile PIREX bottle for collection of the eluted product. The F4 was connected to a 10 L Nalgene PTFE container for collection of the load flowthrough and wash. The F1 was connected to go to a waste 20 L Nalgene container. All the collection vessels were labeled appropriately. The program was ready to start. The method was programmed, any manual actions taken during the purification run was logged in the log record and stated in the "Comments". The target protein eluted at the 2M NaCl lysis buffer wash (Elution block). In the chromatogram window, an absorbance peak detected at a wavelength of 280 nm appeared at the same time as the conductivity increased. Collection was programmed and the method automatically finished. The peak of interest was localised according to the conductivity chromatogram and zoomed in the UV280 profile using the mouse. Three target collection pools were collected: first collection, sample 1 (pool 1); second collection, sample 2 (pool 2); third collection, sample 3 (pool 3). The fractions of interest were transferred into the sterile 500 mL bottles using a sterile 10 mL pipette. The bottles were labeled and stored at 4° C. From each collection one 0.5 mL vial was submitted to QC for HPLC analysis and one 1 mL vial to QC for Endotoxin testing. Twenty percent HAS was added to a final concentration of 0.05% to pool 1, pool 2 and pool 3.

Characterisation of the Recombinant Tat

Western Blot

Figure 11:
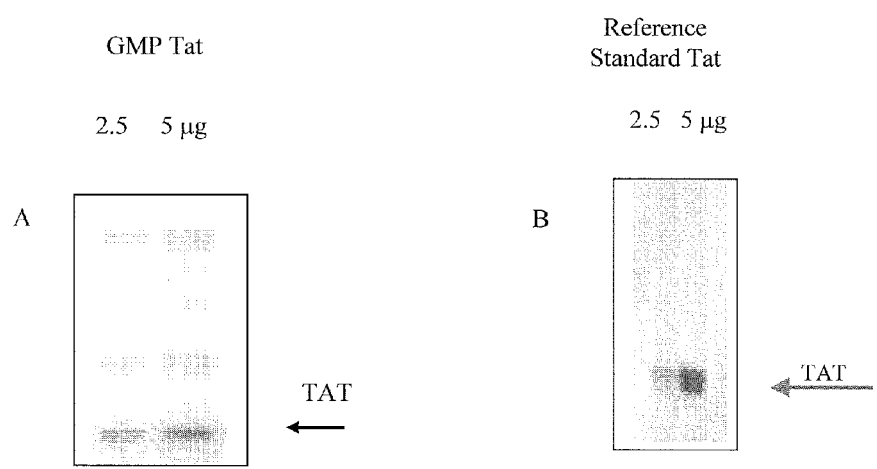
FIG. 11 shows a Western Blot analysis of the GMP Tat (Panel A) in comparison to the Tat protein Reference Standard (Panel B, batch 80802). LMW: low molecular weight standards.

The immunochemical properties of a protein contribute in establishing its identity, homogeneity and purity. Thus, the immunochemical properties of the Tat bulk protein was analysed by Western Blot analysis. Protein samples were separated by SDS page and probed with a primary antibody specific for the Tat protein. After reaction with a polyclonal anti-rabbit HRP conjugate, visualisation of signal was obtained using chemoluminescent reagents. As shown in FIG. 11 (a Western Blot analysis of the GMP Tat versus the Tat Reference Standard), the sample analysed presented a band corresponding to monomeric Tat protein.

Referring to FIG. 11: a Western Blot analysis of the GMP Tat (Panel A) in comparison to the Tat protein Reference Standard (Panel B, batch 80802). LMW: low molecular weight standards.

Molecular Weight

The detection of proteins separated by analytical gel electrophoresis was accomplished by Coomassie Blue staining and Silver staining, which is a more sensitive method. According to these methods, proteins were separated in an electric field under reducing conditions (in the presence of SDS and either 2-mercaptoethanol or dithiothreitol) on the basis of their molecular weight. The results indicate the presence of a single band (>95% of total proteins), corresponding to the monomeric Tat protein. No dimers or higher multiples of the protein were detected.

Tat Biological Activity

Tat biological activity is characterised herein by the ability to be taken up by monocyte-derived dendritic cells (MDDCs). MDDCs are incubated with serial concentrations (0.1-1.000 ng/mL) of the native Tat protein for 10 min and the intracytoplasmatic Tat content evaluated by flow cytometry after staining with specific affinity purified rabbit anti-Tat polyclonal antibodies. The acceptance criteria for MDDCs are as follows:

TABLE 3a

Acceptance criteria for the differentiation of MDDCs

| Cell Membrane Marker | % of positive cells |
| --- | --- |
| HLA-DR | ≥90 |
| CD1a | ≥80 |
| CD83 | ≤20 |
| CD14 | ≤5 | confirmation of Tat biological activity is obtained if the results reported in the table are satisfied at least for three dilution of Tat:

TABLE 3b

| Tat concentration (ng/mL) | % of positive cells |
| --- | --- |
| 0.1 | ≥16 |
| 1 | ≥21 |
| 10 | ≥23 |
| 100 | ≥49 |
| 1000 | ≥72 |

Further, preferred, specifications are summarised as follows:

TABLE 4

| Test | Acceptance Criteria |
| --- | --- |
| Appearance and description | Clear, colorless to slightly yellow liquid |
| pH | 7.5 ± 0.5 |
| Purity and Identity: by Reducing SDS-PAGE Coomassie Blue | Major band migrates to approximately 16 kDa; ≥95% monomer |
| Western Blot | Immunoreactive band comparable to reference |
| SDS-PAGE Silver Stain | Comparable to reference |
| Quantity: Protein concentration by RP-HPLC | >0.158 mg/ml |
| Endotoxin by LAL | <15 EU/µg |
| Bioburden | 0 cfu/piastra |
| Residual Host Cell Proteins | <1% (w/w) |

REFERENCES

Aldovini A, Debouck C, Feinberg M B, Rosenberg M, Arya S K, Wong-Staal F. Synthesis of the complete transactivation gene product of human T-lymphotropic virus type III in *Escherichia coli*: demonstration of immunogenicity in vivo and expression in vitro. Proc Natl Acad Sci USA. 1986, 83:6672-6676.

Arya S K, Guo C, Josephs S F, Wong-Staal F. Transactivator gene of human T-lymphotropic virus type III (HTLV-III). Science 1985, 229:69-73.

Barillari G, Gendelman R, Gallo R C, Ensoli B. The Tat protein of human immunodeficiency virus type 1, a growth factor for AIDS Kaposi sarcoma and cytokine-activated vascular cells, induces adhesion of the same cell types by using integrin receptors recognising the RGD amino acid sequence. Proc Natl Acad Sci USA 1993, 90:7941-7945.

Barillari G, Sgadari C, Fiorelli V, Samaniego F, Colombini S, Manzari V, Modesti A, Nair B C, Cafaro A, Stirrzl M, Ensoli B. The Tat protein of human immunodeficiency virus type-1 promotes vascular cell growth and locomotion by engaging the α5β1 and αvβ3 integrins by mobilising sequestered basic fibroblast growth factor. Blood 1999, 94:663-672.

Brake D A, Debouck C, Biesecker G. Identification of an Arg-Gly-Asp (RGD) cell adhesion site in human immunodeficiency virus type 1 transactivation protein, tat. J Cell Biol 1990, 111:1275-1281.

Burton D R. A vaccine for HIV type 1: the antibody perspective. Proc Natl Acad Sci USA 1997, 94:10018-10023.

Buttò S, Fiorelli V, Tripiciano A, Ruiz-Alvarez M J, Scoglio A, Ensoli F, Ciccozzi M, Collacchi B, Sabbatucci M, Cafaro A, Guzman C A, Borsetti A, Aiuti F, Vardas E, Colvin M, Lukwyia M, Rezza G, Ensoli B, and the Tat Multicentric Study Group. Cross-recognition of the Glade B HIV-1 Tat protein vaccine candidate by antibodies from HIV-1-infected Italian, Ugandan and South African individuals. *J Inf Dis*. In press.

Cafaro A, Caputo A, Fracasso C, Maggiorella M T, Goletti D, Baroncelli S, Pace M, Sernicola L, Koanga-Mogtomo M L, Betti M, Borsetti A, Belli R, Akerblom L, Corrias F, Butte S, Heeney J, Verani P, Titti F, Ensoli B. Control of SHIV-89.6P-infection of cynomolgus monkeys by HIV-1 Tat protein vaccine. *Nat Med* 1999, 5:643-650.

Cafaro A, Caputo A, Maggiorella M T, Baroncelli S, Fracasso C, Pace M, Borsetti A, Sernicola L, Negri D R, Ten Haaft P, Betti M, Michelini Z, Macchia I, Fanales-Belasio E, Belli R, Corrias F, Butte S, Verani P, Titti F, Ensoli B. SHIV89.6P pathogenicity in cynomolgus monkeys and control of viral replication and disease onset by human immunodeficiency virus type 1 Tat vaccine. *J Med Primatol* 2000, 29:193-208.

Cafaro A, Titti F, Fracasso C, Maggiorella M T, Baroncelli S, Caputo A, Goletti D, Borsetti A, Pace M, Fanales-Belasio E, Ridolfi B, Negri D R, Sernicola L, Belli R, Corrias F, Macchia I, Leone P, Michelini Z, ten Haaft P, Buttò S, Verani P, Ensoli B. Vaccination with DNA containing tat coding sequences and unmethylated CpG motifs protects cynomolgus monkeys upon infection with simian/human immunodeficiency virus (SHIV89.6P). *Vaccine* 2001, 19:2862-2877.

Chang, H. K. Gallo R C and Ensoli B. Regulation of Cellular Gene Expression and Function by the Human Immunodeficiency Virus Type 1 Tat Protein. *J Biomed Sci* 1995, 2:189-202.

Chang, H C, Samaniego F, Nair B C, L Buonaguro, and B. Ensoli. HIV-1 Tat protein exits from cells via a leaderless secretory pathway and binds to extracellular matrix-associated heparan sulphate proteoglycans through its basic region. *AIDS* 1997, 11:1421-1431.

Demirhan I, Chandra A, Mueller F et al. Antibody spectrum against the viral transactivator protein in patients with human immunodeficiency virus type 1 infection and Kaposi's sarcoma *J Hum Virol* 2000; 3: 137-43.

Ensoli B, Barillari G, Salahuddin S Z, Gallo R C, Wong-Staal F. Tat protein of HIV-1 stimulates growth of cells derived from Kaposi's sarcoma lesions of AIDS patients. *Nature* 1990, 345:84-86.

Ensoli B, Barillari G, Gallo R C. Cytokines and growth factors in the pathogenesis of AIDS-associated Kaposi's sarcoma. In: Immunol Rev, Moller G. (Eds.), Stockholm 1992, 127:147-155.

Ensoli B, Buonaguro L, Barillari G, Fiorelli V, Gendelman R, Morgan R A, Wingfield P, Gallo R C. Release, uptake, and effects of extracellular human immunodeficiency virus type1 Tat protein on cell growth and viral transactivation. *J Virol* 1993, 67:277-287.

Ensoli B, Gendelman R, Markham P, Fiorelli V, Colombini S, Raffeld M, Cafaro A, Chang H K, Brady J N, Gallo R C. Synergy between basic fibroblast growth factor and HIV-1 Tat protein in induction of Kaposi's sarcoma. *Nature* 1994, 371:674-680.

Fanales-Belasio E, Moretti S, Nappi F, Barillari G, Micheletti F, Cafaro A, Ensoli B. Native HIV-1 Tat protein targets monocyte-derived dendritic cells and enhances their maturation, function and antigen-specific T cell responses. *J Immunol* 2002, 168:197-206.

Fisher A G, Feinberg M B, Josephs S F, Harper M E, Marselle L M, Reyes G, Gonda M A, Aldovini A, Debouk C, Gallo R C, et al. The trans-activator gene of HTLV-III is essential for virus replication. *Nature* 1986, 320:367-371.

Frankel A D, Pabo C O. Cellular uptake of the tat protein from human immunodeficiency virus. *Cell* 1988, 55:1189-1193.

Gavioli R, Gallerani E, Fortini C, Fabris M, Bottoni A, Canella A, Bonaccorsi A, Marastoni M, Micheletti F, Cafaro A, Rimessi P, Caputo A and Ensoli B. HIV-1 Tat protein modulates the generation of cytotoxic T cell epitopes by modifying proteasome composition and enzymatic activity. *J Immunol*, 173:3838-3843, 2004.

Hauber J, Malim M H, Cullen B R. Mutational analysis of the conserved basic domain of human immunodeficiency virus tat protein. *J Virol* 1989, 63:1181-1187.

Kim D T, Mitchell D J, Brockstedt D G, Fong L, Nolan G P, Fathman C G, Engleman E G, Rothbard J B. Introduction of soluble proteins into the MHC class I pathway by conjugation to an HIV tat peptide. *J Immunol* 1997, 159:1666-1668.

Krone W J, Debouck C, Epstein L G, Heutink P, Meloen R, Goudsmit J. Natural antibodies to HIV-tat epitopes and expression of HIV-1 genes in vivo. *J Med Virol* 1988; 26: 261-70.

Lifson J D, Nowak M A, Goldstein S, Rossio J L, Kinter A, Vasquez G, Wiltrout T A, Brown C, Schneider D, Wahl L, Lloyd A L, Williams J, Elkins W R, Fauci A S, Hirsch V M. The extent of early viral replication is a critical determinant of the natural history of simian immunodeficiency virus infection. *J Virol* 1997, 71:9508-9514.

Maggiorella M T, Baroncelli S, Michelini Z, Fanales-Belasio E, Moretti S, Sernicola L, Cara A, Negri D R M, Buttò S, Fiorelli V, Tripiciano A, Scoglio A, Caputo A, Borsetti A, Ridolfi B, Bona R, ten Haaft P, Macchia I, Leone P, Pavone-Cossut M R, Nappi F, Ciccozzi M, Heeney J, Titti F, Cafaro A, and Ensoli B. Long-term protection against SHIV89.6P replication in HIV-1 Tat vaccinated cynomolgus monkeys. *Vaccine*, 22:3258-3269, 2004.

Mellors J W, Rinaldo C R Jr, Gupta P, White R M, Todd J A, Kingsley L A. Prognosis in HIV-1 infection predicted by the quantity of virus in plasma. *Science* 1996, 272: 1167-1170.

Moy P, Daikh Y, Pepinsky B, Thomas D, Fawell S, Barsoum J. Tat-mediated protein delivery can facilitate MHC class I presentation of antigens. *Mol Biotechnol* 1996, 6:105-113.

Myers G, Korber B, Hahn B H, Jeang K T, Mellors J W, McCutchan F E, Henderson L E and Pavlakis G N (eds.). Human Retroviruses and AIDS 1995, Los Alamos, N. Mex.: Los Alamos National Laboratory.

Ratner L, Haseltine W, Patarca R, Livak K J, Starcich B, Josephs S F, Doran E R, Rafalski J A, Whitehorn E A, Baumeister K, Ivanoff L, Petteway S R Jr, Pearson M L, Lautenberger J A, Papas T S, Ghrayeb J, Chang N T, Gallo R C, Wong-Staal F. Complete nucleotide sequence of the AIDS virus, HTLV-III. *Nature* 1985, 313:277-284.

Re M C, Furlini G, Vignoli M, Ramazzotti E, Roderigo G, De Rosa V, Zauli G, Lolli S, Capitani S, La Placa M. *J Acquir Immune Defic. Syndr. Hum. Retrovirol* 1995, 10:408-416.

Re M C, Vignoli M, Furlini G, Gibellini D, Colangeli V, Vitone F, La Placa M. Antibodies against full-length Tat protein and some low-molecular-weight Tat-peptides correlate with low or undetectable viral load in HIV-1 seropositive patients. *J Clin Virol* 2001, 21:81-89.

Reiss P, Lange J M, de Ronde A, de Wolf F, Dekker J, Debouck C, Goudsmit J. Speed of progression to AIDS and degree of antibody response to accessory gene products of HIV-1. *J Med Virol* 1990, 30:163-168.

Rezza G, Fiorelli V, Dorrucci M, Ciccozzi M, Tripiciano A, Scoglio A, Collacchi B, Ruiz-Alvarez M, Giannetto C, Caputo A, Tomasoni L, Castelli F, Sciandra M, Sinicco A, Ensoli F, Buttò, and Ensoli B. The Presence of Anti-Tat Antibodies Is Predictive of Long-Term Non-Progression to AIDS or Severe Immunodeficiency: Findings from a Cohort of HIV Seroconverters. *J Infect Dis, in press.*

Rodman T C, To S E, Hashish H, Manchester K. Epitopes for natural antibodies of human immunodeficiency virus (HIV)-negative (normal) and HIV-positive sera are coincident with two key functional sequences of HIV Tat protein. *Proc Natl Acad Sci USA* 1993, 90:7719-7723.

Rosenberg A H, Lade B N, Chui D S, Lin S W, Dunn J J, Studier F W. Vectors for selective expression of cloned DNAs by T7 RNA polymerase. *Gene.* 1987, 56:125-35.

Roy S, Delling U, Chen C H, Rosen C A, Sonenberg N. A bulge structure in HIV-1 TAR RNA is required for Tat binding and Tat-mediated trans-activation. *Genes Dev* 1990, 4:1365-1373.

Ruben S, Perkins A, Purcell R, Joung K, Sia R, Burghoff R, Haseltine W A, Rosen C A. Structural and functional characterisation of human immunodeficiency virus tat protein. *J Virol* 1989, 63:1-8.

Seigel L J, Ratner L, Josephs S F, Derse D, Feinberg M B, Reyes G R, O'Brien S J, Wong-Staal F. Transactivation induced by human T-lymphotropic virus type III (HTLV III) maps to a viral sequence encoding 58 amino acids and lacks tissue specificity. *Virology.* 1986, 148:226-231.

Sodroski J, Patarca R, Rosen C, Wong-Staal F, Haseltine W. Location of the trans-activating region on the genome of human T-cell lymphotropic virus type III. *Science.* 1985, 229:74-77.

Staprans S I, Dailey P J, Rosenthal A, Horton C, Grant R M, Lerche N, Feinberg M B. Simian immunodeficiency virus disease course is predicted by the extent of virus replication during primary infection. *J Virol* 1999, 73:4829-4839.

Studier F W, Moffatt B A. Use of bacteriophage T7 RNA polymerase to direct selective high-level expression of cloned genes. *J Mol. Biol.* 1986, 189:113-130.

Studier F W, Rosenberg A H, Dunn J J, Dubendorff J W. Use of T7 RNA polymerase to direct expression of cloned genes. *Methods Enzymol.* 1990, 185:60-89.

Ten Haaft P, Verstrepen B, Uberla K, Rosenwirth B, Heeney J. A pathogenic threshold of virus load defined in simian immunodeficiency virus- or simian-human immunodeficiency virus-infected macaques. *J Virol* 1998, 72:10281-10285.

Tyagi M, Rusnati M, Presta M, Giacca M. Internalisation of HIV-1 tat requires cell surface heparan sulphate proteoglycans. *J Biol Chem* 2001, 276:3254-3261

Wahren B, Ljungberg K, Rollman E, Levi M, Zuber B, Kjerrstrom Zuber A, Hinkula J, Leandersson A C, Calarota S, Hejdeman B, Bratt G, Sandstrom E. HIV subtypes and recombination strains—strategies for induction of immune responses in man. *Vaccine* 2002, 20:1988-1993.

Watson A, Ranchalis J, Travis B, McClure J, Sutton W, Johnson P R, Hu S L, Haigwood N L. Plasma viremia in macaques infected with simian immunodeficiency virus: plasma viral load early in infection predicts survival. *J Virol* 1997, 71:284-290.

Wu Y, Marsh J W. Selective transcription and modulation of resting T cell activity by preintegrated HIV DNA. *Science* 2001, 293:1503-1506.

Zagury J F, Sill A, Blattner W, Lachgar A, Le Buanec H, Richardson M, Rappaport J, Hendel H, Bizzini B, Gringeri A, Carcagno M, Criscuolo M, Burny A, Gallo R C, Zagury D. Antibodies to the HIV-1 Tat protein correlated with nonprogression to AIDS: a rationale for the use of Tat toxoid as an HIV-1 vaccine. *J Hum Virol* 1998b, 1:282-292.

SEQUENCE LISTING DESCRIPTION

SEQ ID NOs 1-6 are described above. The pET-3c Vector Sequence is shown in SEQ ID NO. 7. The pLysS Vector Sequence is shown in SEQ ID NO. 8.

SEQUENCE LISTING

```
<160> NUMBER OF SEQ ID NOS: 8

<210> SEQ ID NO 1
<211> LENGTH: 60
<212> TYPE: DNA
<213> ORGANISM: Artificial Sequence
<220> FEATURE:
<223> OTHER INFORMATION: Plasmid pET-3c cloning expression region
<220> FEATURE:
<221> NAME/KEY: misc_feature
<222> LOCATION: (48)..(48)
<223> OTHER INFORMATION: n is a, c, g, or t

<400> SEQUENCE: 1
tctagaaata attttgttta actttaagaa ggagatatac atatatgngg atccggggct      60

<210> SEQ ID NO 2
<211> LENGTH: 352
<212> TYPE: DNA
<213> ORGANISM: Artificial Sequence
<220> FEATURE:
<223> OTHER INFORMATION: Plasmid pET-3c
<220> FEATURE:
<221> NAME/KEY: CDS
```

<222> LOCATION: (63)..(323)

<400> SEQUENCE: 2

```
tgggcgactg aattggtgtc gacatagcag aataggcgtt actcgacaga ggagagcaag        60 aa atg gag cca gta gat cct aga cta gag ccc tgg aag cat cca gga          107
   Met Glu Pro Val Asp Pro Arg Leu Glu Pro Trp Lys His Pro Gly
   1               5                   10                  15 agt cag cct aaa act gct tgt acc aat tgc tat tgt aaa aag tgt tgc         155
Ser Gln Pro Lys Thr Ala Cys Thr Asn Cys Tyr Cys Lys Lys Cys Cys
                20                  25                  30 ttt cat tgc caa gtt tgt ttc ata aca aaa gcc tta ggc atc tcc tat         203
Phe His Cys Gln Val Cys Phe Ile Thr Lys Ala Leu Gly Ile Ser Tyr
            35                  40                  45 ggc agg aag aag cgg aga cag cga cga aga cct cct caa ggc agt cag         251
Gly Arg Lys Lys Arg Arg Gln Arg Arg Arg Pro Pro Gln Gly Ser Gln
        50                  55                  60 act cat caa gtt tct cta tca aag caa ccc acc tcc caa tcc cga ggg         299
Thr His Gln Val Ser Leu Ser Lys Gln Pro Thr Ser Gln Ser Arg Gly
    65                  70                  75 gac ccg aca ggc ccg aag gaa tag aagaagaagg tggagagaga gacagagac         352
Asp Pro Thr Gly Pro Lys Glu
80                  85
```

<210> SEQ ID NO 3
<211> LENGTH: 86
<212> TYPE: PRT
<213> ORGANISM: Artificial Sequence
<220> FEATURE:
<223> OTHER INFORMATION: Synthetic Construct

<400> SEQUENCE: 3

```
Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Arg Pro Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu
                85
```

<210> SEQ ID NO 4
<211> LENGTH: 72
<212> TYPE: DNA
<213> ORGANISM: Artificial Sequence
<220> FEATURE:
<223> OTHER INFORMATION: Figure 5 Cloning of 261 bp of Tat gene
<220> FEATURE:
<221> NAME/KEY: misc_feature
<222> LOCATION: (58)..(58)
<223> OTHER INFORMATION: n is a, c, g, or t

<400> SEQUENCE: 4

```
tctagaaata attttgttta actttaactt taactttaag aaggagatat acatatgnta        60
ggatccgggg ct                                                           72
```

<210> SEQ ID NO 5
<211> LENGTH: 327

<212> TYPE: DNA
<213> ORGANISM: Artificial Sequence
<220> FEATURE:
<223> OTHER INFORMATION: Figure 6 : pET-3c vector
<220> FEATURE:
<221> NAME/KEY: CDS
<222> LOCATION: (22)..(282)

<400> SEQUENCE: 5

```
ctttaagaag gagatataca t atg gag cca gta gat cct aga cta gag ccc        51
                        Met Glu Pro Val Asp Pro Arg Leu Glu Pro
                        1               5                   10 tgg aag cat cca gga agt cag cct aaa act gct tgt acc aat tgc tat        99
Trp Lys His Pro Gly Ser Gln Pro Lys Thr Ala Cys Thr Asn Cys Tyr
            15                  20                  25 tgt aaa aag tgt tgc ttt cat tgc caa gtt tgt ttc ata aca aaa gcc       147
Cys Lys Lys Cys Cys Phe His Cys Gln Val Cys Phe Ile Thr Lys Ala
        30                  35                  40 tta ggc atc tcc tat ggc agg aag aag cgg aga cag cga cga aga cct       195
Leu Gly Ile Ser Tyr Gly Arg Lys Lys Arg Arg Gln Arg Arg Arg Pro
    45                  50                  55 cct caa ggc agt cag act cat caa gtt tct cta tca aag caa ccc acc       243
Pro Gln Gly Ser Gln Thr His Gln Val Ser Leu Ser Lys Gln Pro Thr
60                  65                  70 tcc caa tcc cga ggg gac ccg aca ggc ccg aag gaa tag ggatccggct        292
Ser Gln Ser Arg Gly Asp Pro Thr Gly Pro Lys Glu
75                  80                  85 gctaacaaag cccgaaagga agctgagttg gctgc                                 327
```

<210> SEQ ID NO 6
<211> LENGTH: 86
<212> TYPE: PRT
<213> ORGANISM: Artificial Sequence
<220> FEATURE:
<223> OTHER INFORMATION: Synthetic Construct

<400> SEQUENCE: 6

```
Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Arg Pro Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu
            85
```

<210> SEQ ID NO 7
<211> LENGTH: 4638
<212> TYPE: DNA
<213> ORGANISM: Artificial Sequence
<220> FEATURE:
<223> OTHER INFORMATION: pET-3c Vector Sequence

<400> SEQUENCE: 7

```
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt    180
```

```
gcgggatatc gtccattccg acagcatcgc cagtcactat ggcgtgctgc tagcgctata    240
tgcgttgatg caatttctat gcgcacccgt tctcggagca ctgtccgacc gctttggccg    300
ccgcccagtc ctgctcgctt cgctacttgg agccactatc gactacgcga tcatggcgac    360
cacacccgtc ctgtggatat ccggatatag ttcctccttt cagcaaaaaa cccctcaaga    420
cccgtttaga ggcccaagg ggttatgcta gttattgctc agcggtggca gcagccaact    480
cagcttcctt tcgggctttg ttagcagccg gatccgaccc atttgctgtc caccagtcat    540
gctagccata tgtatatctc cttcttaaag ttaaacaaaa ttatttctag agggaaaccg    600
ttgtggtctc cctatagtga gtcgtattaa tttcgcggga tcgagatctc gatcctctac    660
gccggacgca tcgtggccgg catcaccggc gccacaggtg cggttgctgg cgcctatatc    720
gccgacatca ccgatgggga agatcgggct cgccacttcg ggctcatgag cgcttgtttc    780
ggcgtgggta tggtggcagg ccccgtggcc ggggactgt tgggcgccat ctccttgcat    840
gcaccattcc ttgcggcggc ggtgctcaac ggcctcaacc tactactggg ctgcttccta    900
atgcaggagt cgcataaggg agagcgtcga ccgatgccct tgagagcctt caacccagtc    960
agctccttcc ggtgggcgcg ggcatgact atcgtcgccg cacttatgac tgtcttcttt   1020
atcatgcaac tcgtaggaca ggtgccggca gcgctctggg tcattttcgg cgaggaccgc   1080
tttcgctgga gcgcgacgat gatcggcctg tcgcttgcgg tattcggaat cttgcacgcc   1140
ctcgctcaag ccttcgtcac tggtcccgcc accaaacgtt tcggcgagaa gcaggccatt   1200
atcgccggca tggcggccga cgcgctgggc tacgtcttgc tggcgttcgc gacgcgaggc   1260
tggatggcct tccccattat gattcttctc gcttccggcg gcatcgggat gccgcgttg    1320 caggccatgc tgtccaggca ggtagatgac gaccatcagg gacagcttca aggatcgctc   1380
gcggctctta ccagcctaac ttcgatcact ggaccgctga tcgtcacggc gatttatgcc   1440
gcctcggcga gcacatggaa cgggttggca tggattgtag gcgccgccct ataccttgtc   1500
tgcctccccg cgttgcgtcg cggtgcatgg agccgggcca cctcgacctg aatggaagcc   1560
ggcggcacct cgctaacgga ttcaccactc caagaattgg agccaatcaa ttcttgcgga   1620
gaactgtgaa tgcgcaaacc aacccttggc agaacatatc catcgcgtcc gccatctcca   1680
gcagccgcac gcggcgcatc tcgggcagcg ttgggtcctg ccacgggtg cgcatgatcg    1740 tgctcctgtc gttgaggacc cggctaggct ggcggggttg ccttactggt tagcagaatg   1800
aatcaccgat acgcgagcga acgtgaagcg actgctgctg caaaacgtct gcgacctgag   1860
caacaacatg aatggtcttc ggtttccgtg tttcgtaaag tctggaaacg cggaagtcag   1920
cgccctgcac cattatgttc cggatctgca tcgcaggatg ctgctggcta ccctgtggaa   1980
cacctacatc tgtattaacg aagcgctggc attgaccctg agtgattttt ctctggtccc   2040
gccgcatcca taccgccagt tgtttaccct cacaacgttc cagtaaccgg gcatgttcat   2100
catcagtaac ccgtatcgtg agcatcctct ctcgtttcat cggtatcatt accccccatga  2160 acagaaatcc cccttacacg gaggcatcag tgaccaaaca ggaaaaaacc gcccttaaca   2220
tggcccgctt tatcagaagc cagacattaa cgcttctgga gaaactcaac gagctggacg   2280
cggatgaaca ggcagacatc tgtgaatcgc ttcacgacca cgctgatgag ctttaccgca   2340
gctgcctcgc gcgtttcggt gatgacggtg aaaacctctg acacatgcag ctcccggaga   2400
cggtcacagc ttgtctgtaa gcggatgccg ggagcagaca gcccgtcag ggcgcgtcag    2460 cgggtgttgg cgggtgtcgg ggcgcagcca tgacccagtc acgtagcgat agcggagtgt   2520
```

| | |
|---|---|
| atactggctt aactatgcgg catcagagca gattgtactg agagtgcacc atatatgcgg | 2580 |
| tgtgaaatac cgcacagatg cgtaaggaga aaataccgca tcaggcgctc ttccgcttcc | 2640 |
| tcgctcactg actcgctgcg ctcggtcgtt cggctgcggc gagcggtatc agctcactca | 2700 |
| aaggcggtaa tacggttatc cacagaatca ggggataacg caggaaagaa catgtgagca | 2760 |
| aaaggccagc aaaaggccag gaaccgtaaa aaggccgcgt tgctggcgtt tttccatagg | 2820 |
| ctccgccccc ctgacgagca tcacaaaaat cgacgctcaa gtcagaggtg gcgaaacccg | 2880 |
| acaggactat aaagatacca ggcgtttccc cctggaagct ccctcgtgcg ctctcctgtt | 2940 |
| ccgaccctgc cgcttaccgg atacctgtcc gcctttctcc cttcgggaag cgtggcgctt | 3000 |
| tctcatagct cacgctgtag gtatctcagt tcggtgtagg tcgttcgctc caagctgggc | 3060 |
| tgtgtgcacg aaccccccgt tcagcccgac cgctgcgcct tatccggtaa ctatcgtctt | 3120 |
| gagtccaacc cggtaagaca cgacttatcg ccactggcag cagccactgg taacaggatt | 3180 |
| agcagagcga ggtatgtagg cggtgctaca gagttcttga agtggtggcc taactacggc | 3240 |
| tacactagaa ggacagtatt tggtatctgc gctctgctga gccagttac cttcggaaaa | 3300 |
| agagttggta gctcttgatc cggcaaacaa accaccgctg gtagcggtgg tttttttgtt | 3360 |
| tgcaagcagc agattacgcg cagaaaaaaa ggatctcaag aagatccttt gatcttttct | 3420 |
| acggggtctg acgctcagtg gaacgaaaac tcacgttaag ggattttggt catgagatta | 3480 |
| tcaaaaagga tcttcaccta gatccttta aattaaaaat gaagttttaa atcaatctaa | 3540 |
| agtatatatg agtaaacttg gtctgacagt taccaatgct taatcagtga ggcacctatc | 3600 |
| tcagcgatct gtctatttcg ttcatccata gttgcctgac tccccgtcgt gtagataact | 3660 |
| acgatacggg agggcttacc atctggcccc agtgctgcaa tgataccgcg agacccacgc | 3720 |
| tcaccggctc cagatttatc agcaataaac cagccagccg gaagggccga gcgcagaagt | 3780 |
| ggtcctgcaa ctttatccgc ctccatccag tctattaatt gttgccggga agctagagta | 3840 |
| agtagttcgc cagttaatag tttgcgcaac gttgttgcca ttgctgcagg catcgtggtg | 3900 |
| tcacgctcgt cgtttggtat ggcttcattc agctccggtt cccaacgatc aaggcgagtt | 3960 |
| acatgatccc ccatgttgtg caaaaaagcg gttagctcct tcggtcctcc gatcgttgtc | 4020 |
| agaagtaagt tggccgcagt gttatcactc atggttatgg cagcactgca taattctctt | 4080 |
| actgtcatgc catccgtaag atgcttttct gtgactggtg agtactcaac caagtcattc | 4140 |
| tgagaatagt gtatgcggcg accgagttgc tcttgcccgg cgtcaacacg gataataccg | 4200 |
| cgccacata gcagaacttt aaaagtgctc atcattggaa aacgttcttc ggggcgaaaa | 4260 |
| ctctcaagga tcttaccgct gttgagatcc agttcgatgt aacccactcg tgcacccaac | 4320 |
| tgatcttcag catctttac tttcaccagc gtttctgggt gagcaaaaac aggaaggcaa | 4380 |
| aatgccgcaa aaaagggaat aagggcgaca cggaaatgtt gaatactcat actcttcctt | 4440 |
| tttcaatatt attgaagcat ttatcagggt tattgtctca tgagcggata catatttgaa | 4500 |
| tgtatttaga aaaataaaca ataggggtt ccgcgcacat ttccccgaaa agtgccacct | 4560 |
| gacgtctaag aaaccattat tatcatgaca ttaacctata aaaataggcg tatcacgagg | 4620 |
| ccctttcgtc ttcaagaa | 4638 |

```
<210> SEQ ID NO 8
<211> LENGTH: 4886
<212> TYPE: DNA
<213> ORGANISM: Artificial Sequence
<220> FEATURE:
<223> OTHER INFORMATION: pLysS Vector Sequence
```

<400> SEQUENCE: 8

```
gaattccgga tgagcattca tcaggcgggc aagaatgtga ataaaggccg gataaaactt    60
gtgcttattt ttctttacgg tctttaaaaa ggccgtaata tccagctgaa cggtctggtt   120
ataggtacat tgagcaactg actgaaatgc ctcaaaatgt tctttacgat gccattggga   180
tatatcaacg gtggtatatc cagtgatttt tttctccatt ttagcttcct tagctcctga   240
aaatctcgat aactcaaaaa atacgcccgg tagtgatctt atttcattat ggtgaaagtt   300
ggaacctctt acgtgccgat caacgtctca ttttcgccaa agttggccc agggcttccc    360
ggtatcaaca gggacaccag gatttattta ttctgcgaag tgatcttccg tcacaggtat   420
ttattcggcg caaagtgcgt cgggtgatgc tgccaactta ctgatttagt gtatgatggt   480
gttttgagg tgctccagtg gcttctgttt ctatcagctg tccctcctgt tcagctactg    540
acggggtggt gcgtaacggc aaaagcaccg ccggacatca gcgctagcgg agtgtatact   600
ggcttactat gttggcactg atgagggtgt cagtgaagtg cttcatgtgg caggagaaaa   660
aaggctgcac cggtgcgtca gcagaatatg tgatacagga tatattccgc ttcctcgctc   720
actgactcgc tacgctcggt cgttcgactg cggcgagcgg aaatggctta cgaacggggc   780
ggagatttcc tggaagatgc caggaagata cttaacaggg aagtgagagg ccgcggcaa    840
agccgttttt ccataggctc cgcccccctg acaagcatca cgaaatctga cgctcaaatc   900
agtggtggcg aaacccgaca ggactataaa gataccaggc gtttcccctg gcggctccct   960
cgtgcgctct cctgttcctg cctttcggtt taccggtgtc attccgctgt tatggccgcg  1020
tttgtctcat tccacgcctg acactcagtt ccgggtaggc agttcgctcc aagctggact  1080
gtatgcacga accccccgtt cagtccgacc gctgcgcctt atccggtaac tatcgtcttg  1140
agtccaaccc ggaaagacat gcaaaagcac cactggcagc agccactggt aattgattta  1200
gaggagttag tcttgaagtc atgcgccggt taaggctaaa ctgaaaggac aagttttggt  1260
gactgcgctc ctccaagcca gttacctcgg ttcaaagagt tggtagctca gagaaccttc  1320
gaaaaaccgc cctgcaaggc ggttttttcg ttttcagagc aagagattac gcgcagacca  1380
aaacgatctc aagaagatca tcttattaat cagataaaat atttctagat ttcagtgcaa  1440
tttatctctt caaatgtagc acctgaagtc agccccatac gatataagtt gtaattctca  1500
tgtttgacag cttatcatcg ataagcttta atgcggtagt ttatcacagt taaattgcta  1560
acgcagtcag gcaccgtgta tgaaatctaa caatgcgctc atcgtcatcc tcggcaccgt  1620
caccctggat gctgtaggca taggcttggt tatgccggta ctgccgggcc tcttgcggga  1680
tatcgtccat tccgacagca tcgccagtca ctatggcgtg ctgctagcgc tatatgcgtt  1740
gatgcaattt ctatgcgcac ccgttctcgg agcactgtcc gaccgctttg gccgccgccc  1800
agtcctgctc gcttcgctac ttggagccac tatcgactac gcgatcatgg cgaccacacc  1860
cgtcctgtgg atccggccca ttggctgcct cccacacttg gatatgcctc tcggagcct   1920
tatagaattg tttataagac ttgcgcatta tttgacctcc aatgcgaaca aagggaaacc  1980
gctgtggtct cccttttagtg agttcaatta attatccacg gtcagaagtg accagttcgt  2040
tcttctccca ccaacgctta aggtcgaacg aagggcaagc cttcggcgcc acctcatgat  2100
gggcgcgaag accagcgcct tcgtacttag ccagcagtgt gacaagcagt gagcgaaggg  2160
attgcatttg ggctggcgta aagttagcgt cgaacttacc tttatcgtcg ataccaccaa  2220
caaggcagac gccgatagag ttgtggttgt aacccttagc gtgagagcct acagccatct  2280
```

```
catctcgtcc tgcctccaca gtaccgtctc gcttgatgat aaagtggtat cccacatcga    2340
gccaaccctg ctctttgtgc cactggcgaa tctcacggac accaacattc tgacttggct    2400
tggtagccga gcagtgaaca aagattgcgt cagtagattc acgttgttta aactgtacac    2460
gagccattat ttcttcctc cttccttt taatctatca aggggaccc ggatcctcta        2520
cgccggacgc atcgtggccg gcatcaccgg cgccacaggt gcggttgctg gcgcctatat    2580
cgccgacatc accgatgggg aagatcgggc tcgccacttc gggctcatga gcgcttgttt    2640
cggcgtgggt atggtggcag gccccgtggc cgggggactg ttgggcgcca tctccttgca    2700
tgcaccattc cttgcggcgg cggtgctcaa cggcctcaac ctactactgg gctgcttcct    2760
aatgcaggag tcgcataagg gagagcgtcg accgatgccc ttgagagcct tcaacccagt    2820
cagctccttc cggtgggcgc ggggcatgac tatcgtcgcc gcacttatga ctgtcttctt    2880
tatcatgcaa ctcgtaggac aggtgccggc agcgctctgg gtcattttcg gcgaggaccg    2940
ctttcgctgg agcgcgacga tgatcggcct gtcgcttgcg gtattcggaa tcttgcacgc    3000
cctcgctcaa gccttcgtca ctggtcccgc caccaaacgt tcggcgaga  agcaggccat    3060
tatcgccggc atggcggccg acgcgctggg ctacgtcttg ctggcgttcg cgacgcgagg    3120
ctggatggcc ttccccatta tgattcttct cgcttccggc ggcatcggga tgcccgcgtt    3180
gcaggccatg ctgtccaggc aggtagatga cgaccatcag ggacagcttc aaggatcgct    3240
cgcggctctt accagcctaa cttcgatcac tggaccgctg atcgtcacgg cgatttatgc    3300
cgcctcggcg agcacatgga acgggttggc atggattgta ggcgccgccc tataccttgt    3360
ctgcctcccc gcgttgcgtc gcggtgcatg gagccgggcc acctcgacct gaatggaagc    3420
cggcggcacc tcgctaacgg attcaccact ccaagaattg gagccaatca attcttgcgg    3480
agaactgtga atgcgcaaac caacccttgg cagaacatat ccatcgcgtc cgccatctcc    3540
agcagccgca cgcggcgcat ctcgggcagc gttgggtcct ggccacgggt gcgcatgatc    3600
gtgctcctgt cgttgaggac ccggctaggc tggcggggtt gccttactgg ttagcagaat    3660
gaatcaccga tacgcgagcg aacgtgaagc gactgctgct gcaaaacgtc tgcgacctga    3720
gcaacaacat gaatggtctt cggtttccgt gttcgtaaa gtctggaaac gcggaagtcc     3780
cctacgtgct gctgaagttg cccgcaacag agagtggaac caaccggtga taccacgata    3840
ctatgactga gagtcaacgc catgagcggc ctcatttctt attctgagtt acaacagtcc    3900
gcaccgctgt ccggtagctc cttccggtgg gcgcggggca tgactatcgt cgccgcactt    3960
atgactgtct tctttatcat gcaactcgta ggacaggtgc cggcagcgcc caacagtccc    4020
ccggccacgg ggcctgccac catacccacg ccgaaacaag cgccctgcac cattatgttc    4080
cggatctgca tcgcaggatg ctgctggcta ccctgtggaa cacctacatc tgtattaacg    4140
aagcgctaac cgttttttatc aggctctggg aggcagaata aatgatcata tcgtcaatta    4200
ttacctccac ggggagagcc tgagcaaact ggcctcaggc atttgagaag cacacggtca    4260
cactgcttcc ggtagtcaat aaaccggtaa accagcaata gacataagcg gctatttaac    4320
gaccctgccc tgaaccgacg accgggtcga atttgctttc gaatttctgc cattcatccg    4380
cttattatca cttattcagg cgtagcacca ggcgtttaag ggcaccaata actgccttaa    4440
aaaaattacg ccccgccctg ccactcatcg cagtactgtt gtaattcatt aagcattctg    4500
ccgacatgga agccatcaca gacggcatga tgaacctgaa tcgccagcgg catcagcacc    4560
ttgtcgccct gcgtataata tttgcccatg gtgaaaacgg gggcgaagaa gttgtccata    4620
ttggccacgt ttaaatcaaa actggtgaaa ctcacccagg gattggctga gacgaaaaac    4680
```

```
atattctcaa taaacccttt agggaaatag gccaggtttt caccgtaaca cgccacatct    4740
tgcgaatata tgtgtagaaa ctgccggaaa tcgtcgtggt attcactcca gagcgatgaa    4800
aacgtttcag tttgctcatg gaaaacggtg taacaagggt gaacactatc ccatatcacc    4860
agctcaccgt ctttcattgc catacg                                         4886
```

The invention claimed is:

1. A process for the preparation of biologically active Tat suitable for human use, comprising the steps of:
   1) culturing a host organism capable of expressing Tat when induced in a culture volume of at least 15 L, wherein the host organism is *Escherichia coli*, and wherein the Tat comprises the amino acid sequence set forth in SEQ ID NO: 3, or a mutant or variant thereof having biological activity comparable with biologically active Tat and having at least 70% sequence homology to said sequence;
   2) culturing said host organism in a culture media that comprises a vegetable peptone and does not comprise components of animal origin;
   3) inducing the expression of Tat during the logarithmic growth phase of the host organism; wherein the induction occurs at 0.6 OD of the host culture,
   4) purifying Tat from the culture, wherein the yield is at least 15.8 mg of Tat for a culture volume of 15 L; and wherein the Tat produced is considered biologically active if at a concentration of 100 ng/ml it is taken up by at least 49% of a cell culture of monocyte-derived dendritic cells (MDDC).

2. The process of claim 1, wherein the host organism is a BL21 strain of *Escherichia coli*.

3. The process of claim 1, wherein the host organism has been transformed using a suitable expression plasmid.

4. The process of claim 1, wherein said Tat comprises a Tat-encoding sequence under the control of an inducible promoter.

5. The process of claim 4, wherein the inducible promoter is recognised by a polymerase, wherein said polymerase is under the control of an inducible promoter.

6. The process of claim 4, wherein the inducible promoter is a lac promoter.

7. The process of any of claims 4 to 6, wherein the Tat encoding sequence is under the control of a T7 promoter.

8. The process of claim 7, wherein the host organism is capable of expressing T7 RNA polymerase.

9. The process of claim 1, wherein the amino acid sequence is encoded by the nucleic acid sequence set forth in SEQ ID NO: 2.

* * * * *